United States Patent
Madhavan et al.

(10) Patent No.: US 10,600,503 B2
(45) Date of Patent: Mar. 24, 2020

(54) SYSTEMS MEDICINE PLATFORM FOR PERSONALIZED ONCOLOGY

(75) Inventors: Subha Madhavan, Rockville, MD (US); Michael A. Harris, Silver Spring, MD (US); Yuriy Gusev, Rockville, MD (US); Andrew Shinohara, Washington, DC (US); David M. Tanenbaum, Vienna, VA (US); Kevin Rosso, Annapolis, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 301 days.

(21) Appl. No.: 14/236,796

(22) PCT Filed: Aug. 3, 2012

(86) PCT No.: PCT/US2012/049540
§ 371 (c)(1),
(2), (4) Date: Jul. 28, 2014

(87) PCT Pub. No.: WO2013/020058
PCT Pub. Date: Feb. 7, 2013

(65) Prior Publication Data
US 2014/0330583 A1    Nov. 6, 2014

Related U.S. Application Data

(60) Provisional application No. 61/515,185, filed on Aug. 4, 2011.

(51) Int. Cl.
*G16H 10/60* (2018.01)
*G16B 50/00* (2019.01)
(Continued)

(52) U.S. Cl.
CPC .............. *G16H 10/60* (2018.01); *G16B 50/00* (2019.02); *G16B 40/00* (2019.02); *G16B 45/00* (2019.02)

(58) Field of Classification Search
CPC ........ G01N 33/50; G01N 33/57; G06F 19/18; G06F 19/24; G06F 19/00; G06Q 50/22;
(Continued)

(56) References Cited

U.S. PATENT DOCUMENTS

2006/0020398 A1 * 1/2006 Vernon .................. G06F 19/20 702/20
2006/0136143 A1 * 6/2006 Avinash ................. G06F 19/28 702/20
(Continued)

OTHER PUBLICATIONS

Gentleman, R. C., et. al., "Bioconductor: open software development for computational biology and bioinformatics". Genome Biol. 5(10): R80. (2004).
(Continued)

*Primary Examiner* — Joseph D Burgess
(74) *Attorney, Agent, or Firm* — Blank Rome LLP

(57) ABSTRACT

The present invention is directed to a platform (e.g., Web-based) that enables basic and clinical research activities by integrating patient characteristics and clinical outcome data with a variety of high-throughput research data in a unified environment. While several rich data repositories for high dimensional research data exist in the public domain, most focus on a single data type and do not support integration across multiple technologies. The present invention in at least one embodiment includes a broad collection of bioinformatics and systems biology tools for analysis and visualization of four major "omics" types: DNA, mRNA, microRNA, and metabolites, as well as next-generation sequencing. The present invention helps facilitate systems medicine by providing easy identification of trends and
(Continued)

patterns in integrated datasets and hence facilitate the use of better targeted therapies for cancer.

20 Claims, 19 Drawing Sheets

(51) Int. Cl.
G16B 40/00 (2019.01)
G16B 45/00 (2019.01)

(58) Field of Classification Search
CPC ........ G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00; G16H 50/20; G16H 50/30; C12Q 1/6886
See application file for complete search history.

(56) References Cited

U.S. PATENT DOCUMENTS

| | | | | |
|---|---|---|---|---|
| 2008/0082522 | A1* | 4/2008 | Jung | G06F 19/326 |
| 2010/0285995 | A1* | 11/2010 | Russo | C12Q 1/6886 506/16 |
| 2013/0058992 | A1* | 3/2013 | Godwin | C12Q 1/6886 424/450 |

OTHER PUBLICATIONS

Calin, G. A., and Croce, C. M. (2006). "MicroRNA signatures in human cancers". Nat Rev Cancer. 6, 857-66.
Hennessy, E., and O'Driscoll, L. (2008). "Molecular medicine of microRNAs: structure, function and implications for diabetes". Expert Rev Mol Med. 10, e24.
Callis, T. E. E., and Wang, D.-Z. Z. (2008). "Taking microRNAs to heart". Trends Mol Med. 14, 254-60.
Uchida, S., et al., "Characterization of the vulnerability to repeated stress in Fischer 344 rats: possible involvement of microRNA-mediated down-regulation of the glucocorticoid receptor". Eur J Neurosci. 27, 2250-61, (2008).
Griffiths-Jones, S., et al., "miRBase: microRNA sequences, targets and gene nomenclature". Nucleic Acids Res. 34, D140-4. (2006).
Friedman, R.C., et al. (2009). "Most mammalian mRNAs are conserved targets of microRNAs". Genome Res. 19, 92-105.
Brase, J., et al., "Serum microRNAs as non-invasive biomarkers for cancer". Mol Cancer. 9:306. (2010).
Huang, Z., Huang, et. al., (2010). "Plasma microRNAs are promising novel biomarkers for early detection of colorectal cancer". Int J Cancer. 127(1):118-26.
Castle, A.L.; et al., "Metabolomics Standards Workshop and the development of International standards for reporting metabolomics experimental results", Submitted Dec. 20, 2005; Briefings in Bioinformatics. vol. 7 No. 2 pp. 159-165.
Kuo, K.-T. T., et al., (2009). "Analysis of DNA copy number alterations in ovarian serous tumors identifies new molecular genetic changes in low-grade and high-grade carcinomas". Cancer Res. 69(12):5267.
S Saldanha, A. J. (2004). "Java treeview: extensible visualization of microarray data". Bioinformatics. 20(17):3246-8.
Shannon, P., Markiel, A., Ozier, O., Baliga, N. S., Wang, J. T., Ramage, D., Amin, N., Schwikowski, B., and Ideker, T. (2003). Cytoscape: "A software environment for integrated models of biomolecular interaction networks". Genome Res. 13(11):2498-504.
Skinner, M. E., Uzilov, A. V., Stein, L. D., Mungall, C. J., and Holmes, I. H. (2009). JBrowse: A next-generation genome browser. Genome Res. 19(9):1630-8.
Barrett, T., Suzek, T. O., Troup, D. B., Wilhite, S. E., Ngau, W.-C. C., Ledoux, P., Rudnev, D., Lash, A. E., Fujibuchi, W., and Edgar, R. (2005). NCBI GEO: mining millions of expression profiles-database and tools. Nucleic Acids Res. 33, D562-D566.
Parkinson, H., Sarkans, U., Shojatalab, M., Abeygunawardena, N., Contrino, S., Coulson, R., Farne, A., Lara, G. G., Holloway, E., Kapushesky, M., Lilja, P., Mukherjee, G., Oezcimen, A., Rayner, T., Rocca-Serra, P., Sharma, A., Sansone, S., and Brazma, A. (2005). ArrayExpress—a public repository for microarray gene expression data at the EBI. Nucleic Acids Res. 33, D553-D555.
Irizarry, R. A., Bolstad, B. M., Collin, F., Cope, L. M., Hobbs, B., and Speed, T. P. (2003). Summaries of affymetrix GeneChip probe level data. Nucleic Acids Res. 31(4):e15.
Bolstad, B. M., Irizarry, R. A., Astrand, M., and Speed, T. P. (2003). A comparison of normalization methods for high density oligonucleotide array data based on variance and bias. Bioinformatics. 19(2):185-193.
Wright, G. W., and Simon, R. M. (2003). A random variance model for detection of differential gene expression in small microarray experiments. Bioinformatics. 19: 2448-55.
Iorio, M. V., Visone, R., Di Leva, G., Donati, V., Petrocca, F., Casalini, P., Taccioli, C., Volinia, S., Liu, C. G., Alder, H., Calin, G. A., Ménard, S., and Croce, C. M, (2007). MicroRNA signatures in human ovarian cancer. Cancer Res. 67:8699-8707.
Livak, K. J., and Schmittgen, T. D. (2001). Analysis of relative gene expression data using real-time quantitative PCR and the 2(-Delta delta C(T)) method. Methods. 25(4):402-8.
Schmittgen, T. D., Lee, E. J. J., Jiang, J., Sarkar, A., Yang, L., Elton, T. S., and Chen, C. (2008). Real-time PCR quantification of precursor and mature microRNA. Methods. 44(1):31-8.
Kozomara, A., and Griffiths-Jones, S. (2011). miRBase: integrating microRNA annotation and deep-sequencing data. Nucleic Acids Res. D152-7.
Pedrioli, P. G. A., Eng, J. K., Hubley, R., Vogelzang, M., Deutsch, E. W., Raught, B., Pratt, B., Nilsson, E., Angeletti, R. H., Apweiler, R., Cheung, K., Costello, C. E., Hermjakob, H., Huang, S., Julian, R. K., Kapp, E., McComb, M. E., Oliver, S. G., Omenn, G., Paton, N. W., Simpson, R., Smith, R., Taylor, C. F., Zhu, W., and Aebersold, R. (2004). A common open representation of mass spectrometry data and its application to proteomics research. Nat Biotech. 22:1459-1466.
Li, C. and Wong, W.H. (2003). DNA-Chip Analyzer (dChip). In the analysis of gene expression data: methods and software. Edited by G Parmigiani, ES Garrett, R Irizarry and SL Zeger. Springer, New York. 120-141.
Yuanjian Feng, Guoqiang Yu, Tian-Li Wang, Ie-Ming Shih, and Yue Wang (2010). Analyzing DNA copy number changes using fused margin regression. Intl J of Functional Informatics and Personalized Medicine. vol. 3, No. 1, pp. 3-15.
Loi, S., Haibe-Kains, B., Desmedt, C., Wirapati, P., Lallemand, F., Tutt, A. M., Gillet, C., Ellis, P., Ryder, K., Reid, J. F., Daidone, M. G., Pierotti, M. A., Berns, E. M. M., Jansen, M. P. P., Foekens, J. A., Delorenzi, M., Bontempi, G., Piccart, M, J., and Sotiriou, C. (2008). Predicting prognosis using molecular profiling in estrogen receptor-positive breast cancer treated with tamoxifen. BMC Genomics. 9:239.
Sotiriou, C., Wirapati, P., Loi, S., Harris, A., Fox, S., Smeds, J., Nordgren, H., Farmer, P., Praz, V., Haibe-Kains, B., Desmedt, C., Larsimont, D., Cardoso, F., Peterse, H., Nuyten, D., Buyse, M., Van de Vijver, M. J., Bergh, J., Piccart, M., and Delorenzi, M. (2006). Gene expression profiling in breast cancer: understanding the molecular basis of histologic grade to improve prognosis. J Natl Cancer Inst. 98(4):262-72.
Raychaudhuri, S., Stuart, J. M., and Altman, R. B. (2000). Principal components analysis to summarize microarray experiments: application to sporulation time series. Pac Symp Biocomput. 455-66.

(56) References Cited

OTHER PUBLICATIONS

Golay J, Loffarelli L, Luppi M, Castellano M and Introna M (1994). The human A-myb protein is a strong activator of transcription. Oncogene. 9(9):2469-79.

Kaplan, E. L., and Meier, P. (1958). Nonparametric estimation from incomplete observations. J Amer Statist Assn. 53:457-481.

Szklarczyk, D., Franceschini, A., Kuhn, M., Simonovic, M., Roth, A., Minguez, P., Doerks, T., Stark, M., Muller, J., Bork, P., Jensen, L. J., and von Mering, C. (2011). The STRING database in 2011: functional interaction networks of proteins, globally integrated and scored. Nucleic Acids Res. 39:D561-8.

Rebhan, M., Chalifa-Caspi, V., Prilusky, J., and Lancet, D. (1997). GeneCards: integrating information about genes, proteins and diseases. Trends Genet. 13(4):163.

Wu CH, Huang H, Arminski L, Castro-Alvear J, Chen Y, Hu ZZ, Ledley RS, Lewis KC, Mewes HW, Orcutt BC, Suzek BE, Tsugita A, Vinayaka CR, Yeh LS, Zhang J, and Barker WC (2002). The Protein Information Resource: an integrated public resource of functional annotation of proteins. Nucleic Acids Res. 30(1):35-7.

Online Mendelian Inheritance in Man, OMIM (TM). McKusick-Nathans Institute of Genetic Medicine, Johns Hopkins University (Baltimore, MD) and National Center for Biotechnology Information, National Library of Medicine (Bethesda, MD). <http://www.ncbi.nlm.nih.gov/omim/>.

Sherry, S. T., Ward, M. H., Kholodov, M., Baker, J., Phan, L., Smigielski, E. M., and Sirotkin, K. (2001). dbSNP: the NCBI database of genetic variation. Nucleic Acids Res. 29(1):308-11.

Sircoulomb, F., Bekhouche, I., Finetti, P., Adelaide, J., Hamida, A. B., Bonansea, J., Raynaud, S., Innocenti, C., Charafe-Jauffret, E., Tarpin, C., Ayed, F. B., Viens, P., Jacquemier, J., Bertucci, F., Birnbaum, D., and Chaffanet, M. (2010). Genome profiling of ERBB2-amplified breast cancers. BMC Cancer. 10:539.

Chuang, H.-Y. Y., Lee, E., Liu, Y.-T. T., Lee, D., and Ideker, T. (2007). Network-based classification of breast cancer metastasis. Mol Syst Biol. 3:140.

Reymond, M.A. and Schlegel, W. (2007): Proteomics in cancer. Adv Clin Chem. 44:103-142.

Chin, L., and Gray, J. W. (2008). Translating insights from the cancer genome into clinical practice. Nature. 452:553-563.

Roukos DH (2010). Systems medicine: a real approach for future personalized oncology? Pharmacogenomics. 11 (3):283-287.

Madhavan, S., Zenklusen, J.-C., Kotliarov, Y., Sahni, H., Fine, H. A., and Buetow, K. (2009). Rembrandt: Helping personalized medicine become a reality through integrative translational research. Mol Cancer Res. 7(2):157-167.

Weston, A. D., and Hood, L. (2004). Systems biology, proteomics, and the future of health care: toward predictive, preventative, and personalized medicine. J Proteome Res. 3(2):179-196.

Auffray, C., Chen, Z., and Hood, L. (2009). Systems medicine: the future of medical genomics and healthcare, Genome Med. 1(1):2.

Rhodes, D. R., Yu, J., Shanker, K., Deshpande, N., Varambally, R., Ghosh, D., Barrette, T., Pandey, A., and Chinnaiyan, A. M. (2004). ONCOMINE: a cancer microarray database and integrated data-mining platform. Neoplasia. 6(1):1-6.

Sherlock, G., Hernandez-Boussard, T., Kasarskis, A., Binkley, G., Matese, J. C., Dwight, S. S., Kaloper, M., Weng, S., Jin, H., Ball, C. A., Eisen, M. B., Spellman, P. T., Brown, P. O., Botstein, D., and Cherry, J. M. (2001). The Stanford microarray database. Nucleic Acids Res, 29(1):152-5.

Madhavan S, Sander A, Chou W-Y, Shuster A, Boone K, Dente M, Shad A and Hesse B (2011). Pediatric Palliative Care in the Age of eHealth: Opportunities for Advances in HIT to Improve Patient-Centered Communication. Am J Prev Medicine. 40 (5) Supplement 2: S208-S216.

\* cited by examiner

Current Study: BRC_LOI_2008_01

List Name: [RelapseFreePts] [Save Selected]

Patient Search Results

| | GDOC_ID | AGE | CHIP_TYPE | DISEASE_FREE_SURVIVAL | DMFS_DAYS | ELSTON_ELL | ER_STATUS | EVENT_DFS | EVENT_DMF | NODAL_STA | PGR_STATU | TAMOXIFEN |
|---|---|---|---|---|---|---|---|---|---|---|---|---|
| ☑ | 116393 | 67 | HG-U133Plu | 4222 | 4222 | 2 | POSITIVE | CENSORING | CENSORING | POSITIVE | NEGATIVE | YES |
| ☑ | 116391 | 76 | HG-U133Plu | 2622 | 2622 | 3 | POSITIVE | CENSORING | CENSORING | NEGATIVE | POSITIVE | YES |
| ☑ | 116389 | 48 | HG-U133Plu | 3973 | 3973 | 3 | POSITIVE | CENSORING | CENSORING | NEGATIVE | NEGATIVE | YES |
| ☑ | 116387 | 70 | HG-U133Plu | 3751 | 3751 | 2 | POSITIVE | EVENT | EVENT | POSITIVE | POSITIVE | YES |
| ☑ | 116385 | 67 | HG-U133Plu | 3211 | 3211 | 3 | POSITIVE | CENSORING | CENSORING | POSITIVE | NEGATIVE | YES |
| ☑ | 116381 | 77 | HG-U133Plu | 2750 | 2750 | 1 | POSITIVE | CENSORING | CENSORING | POSITIVE | POSITIVE | YES |
| ☑ | 116379 | 81 | HG-U133Plu | 2278 | 2278 | 2 | POSITIVE | CENSORING | CENSORING | NEGATIVE | NEGATIVE | YES |
| ☑ | 116373 | 79 | HG-U133Plu | 4454 | 4454 | 1 | POSITIVE | CENSORING | CENSORING | NEGATIVE | POSITIVE | YES |
| ☑ | 116371 | 72 | HG-U133Plu | 2263 | 2263 | 2 | POSITIVE | CENSORING | CENSORING | NEGATIVE | POSITIVE | YES |
| ☑ | 116369 | 60 | HG-U133Plu | 4554 | 4554 | 1 | POSITIVE | CENSORING | CENSORING | POSITIVE | POSITIVE | YES |
| ☑ | 116367 | 57 | HG-U133Plu | 4596 | 4596 | 1 | POSITIVE | CENSORING | CENSORING | POSITIVE | NEGATIVE | YES |
| ☑ | 116365 | 64 | HG-U133Plu | 4514 | 4514 | 2 | POSITIVE | CENSORING | CENSORING | NEGATIVE | POSITIVE | YES |
| ☑ | 116363 | 74 | HG-U133Plu | 3429 | 3429 | 3 | POSITIVE | CENSORING | CENSORING | POSITIVE | POSITIVE | YES |
| ☑ | 116361 | 58 | HG-U133Plu | 4481 | 4481 | 1 | POSITIVE | CENSORING | CENSORING | POSITIVE | POSITIVE | YES |
| ☑ | 116357 | 73 | HG-U133Plu | 3349 | 3349 | 3 | POSITIVE | CENSORING | CENSORING | POSITIVE | POSITIVE | YES |

|← <<|Page [1] of 18|>> →| [25 ▽]     View 1-25 of 432

Export results

Perform Group Comparison Analysis

Current Study: BRC_LOI_2008_01    change study?
Select a baseline group and a comparison group(s)

Select a baseline group: [Loi-E-NN-ER-T ▼]

Select comparison group: [Loi-C-NN-ER-T ▼]

p-value:
[.05]

Fold Change:
[1.4]

Statistical Method:
[T-Test: Two Sample Test ▼]

Multiple Comparison Adjustment:
[None ▼]

Data-Type: [GENE EXPRESSION ▼]

Dataset:
[U133A RMA Normalization ▼]

[Submit Analysis]

FIG. 13B

Analysis Results

| Statistical Method | TTest |
| Adjustment | NONE |
| Fold Change | 1.4 |
| Pvalue | .05 |
| Study | BRC_LOI_2008_01 |
| Data File | HG-U133A_6532.Rda |
| Baseline Group | Loi-E-NN-ER-T |
| Groups | Loi-C-NN-ER-T |

List Name: [        ]    [Save Selected ▼]

view HeatMap for selected reporters

Analysis Results

| Reporter ID | Gene Symbol | p-value | Fold Change |
|---|---|---|---|
| ☑ 213906_at | MYBL1 | $1.570 \times 10^{-6}$ | -2.508 |
| ☑ 219494_at | RAD54B | $3.227 \times 10^{-6}$ | -1.570 |
| ☑ 215828_at |  | $9.060 \times 10^{-6}$ | -1.407 |
| ☑ 213310_at | EIF2C2 | $9.658 \times 10^{-6}$ | -1.428 |
| ☑ 201860_s_at | PLAT | $4.879 \times 10^{-5}$ | 2.192 |
| ☑ 208451_s_at | C4A | $5.928 \times 10^{-5}$ | 2.061 |

| Analysis Results | | | |
|---|---|---|---|
| ☐ Reporter ID | Gene Symbol | p-value ⇕ | Fold Change |
| ☐ 213906_at | MY... | Perform Gene Expression KM ▶ | 508 |
| ☐ 219494_at | RA... | Perform Gene Expression Search | 570 |
| ☐ 215828_at | | Search in Entrez | 407 |
| ☐ 213310_at | EIF... | Search in iHOP | 428 |
| ☐ 201860_s_at | PL... | Search in PIR | 92 |
| ☐ 208451_s_at | C4... | Search in Ensembl Gene View | 51 |
| ☐ 214428_x_at | C4... | Search in Reactome | 13 |
| ☐ 208683_x_at | CA... | View at KEGG | 40 |
| ☐ 210021_s_at | CC... | View at QuickGO | 69 |
| ☐ 222380_s_at | PD... | View at GeneCards | 54 |
| ☐ 201195_s_at | SL... | View at String DB | 76 |
| ☐ 214782_at | CTTN | $2.570 \times 10^{-4}$ | -1.519 |

FIG. 15

SYSTEMS MEDICINE PLATFORM FOR PERSONALIZED ONCOLOGY

REFERENCE TO RELATED APPLICATION

The present application is a National Stage of International Application No. PCT/US2012/049540, filed Aug. 3, 2012, and claims the benefit of U.S. Provisional Patent Application No. 61/515,185, filed Aug. 4, 2011, whose disclosures are hereby incorporated by reference in their entirety into the present disclosure.

STATEMENT OF GOVERNMENT INTEREST

This invention was made with government support under Grant No. HHSN261200800001E awarded by National Institutes of Health. The government has certain rights in the invention.

FIELD OF THE INVENTION

The present invention is directed to a computer-implemented system and method for providing data relating to cancer and more particularly to such a system and method in which data from disparate technologies are normalized and integrated into a database.

DESCRIPTION OF RELATED ART

Currently, cancer therapy remains limited by a "one-size-fits-all" approach, whereby treatment decisions are based mainly on the clinical stage of disease, yet fail to reference the individual's underlying biology and its role in driving malignancy. Identifying better personalized therapies for cancer treatment is hindered by the lack of high quality "omics" data of sufficient size to produce meaningful results, and the ability to integrate biomedical data from disparate technologies. Resolving these issues will help translation of therapies from a research to a clinical care setting by helping clinicians develop patient-specific treatments based on the unique signatures in each patient's tumor.

With the sequencing of the human genome and availability of high power computational methods and a variety of high throughput "omics" technologies (e.g., genomics, transcriptomics and metabolomics), cancer research and care are poised to undergo revolutionary change. These new technologies and approaches have fueled the rise of Systems Biology, which is now fully established as a discipline. The new and emerging field of Systems Medicine, an application of Systems Biology approaches to biomedical problems in the clinical setting, leverages complex computational tools and high dimensional data to derive personalized assessments of disease risk. Systems Medicine offers the potential for more effective individualized diagnosis, prognosis, and treatment options. Achieving this goal requires the effective use of petabytes of data, which necessitates the development of both new types of tools and a new type of physician—one with a grasp of modern computational sciences, "omics" technologies, and a systems approach to the practice of medicine. As part of this transformation, clinicians will need views of integrated biomedical data from disparate sources, and will begin to utilize validated in silico methodologies for analysis. A critical factor in the success of Systems Medicine will be the ease with which high-quality, high-dimensional data can be integrated, redistributed and analyzed both within and across functional domains.

Throughout the present disclosure, bracketed numbers refer to the following references, whose disclosures are hereby incorporated by reference in their entireties into the present disclosure:

1. Gentleman, R. C., Carey, V. J., Bates, D. M., Bolstad, B., Dettling, M., Dudoit, S., Ellis, B., Gautier, L., Ge, Y., Gentry, J., Hornik, K., Hothorn, T., Huber, W., Iacus, S., Irizarry, R., Leisch, F., Li, C., Maechler, M., Rossini, A. J., Sawitzki, G., Smith, C., Smyth, G., Tierney, L., Yang, J. Y., and Zhang, J. (2004). Bioconductor: open software development for computational biology and bioinformatics. *Genome Biol.* 5(10): R80.

2. Calin, G. A., and Croce, C. M. (2006). MicroRNA signatures in human cancers. *Nat Rev Cancer.* 6, 857-66.

3. Hennessy, E., and O'Driscoll, L. (2008). Molecular medicine of microRNAs: structure, function and implications for diabetes. *Expert Rev Mol Med.* 10, e24.

4. Callis, T. E. E., and Wang, D.-Z. Z. (2008). Taking microRNAs to heart. *Trends Mol Med.* 14, 254-60.

5. Uchida, S., Nishida, A., Hara, K., Kamemoto, T., Suetsugi, M., Fujimoto, M., Watanuki, T., Wakabayashi, Y., Otsuki, K., McEwen, B. S., and Watanabe, Y. (2008). Characterization of the vulnerability to repeated stress in fischer 344 rats: possible involvement of microRNA-mediated down-regulation of the glucocorticoid receptor. *Eur J Neurosci.* 27, 2250-61

6. Griffiths-Jones, S., Grocock, R. J., van Dongen, S., Bateman, A., and Enright, A. J. (2006). miRBase: microRNA sequences, targets and gene nomenclature. *Nucleic Acids Res.* 34, D140-4.

7. Friedman, R. C., Farh, K. K., Burge, C. B., and Bartel, D. P. (2009). Most mammalian mRNAs are conserved targets of microRNAs. *Genome Res.* 19, 92-105.

8. Brase, J., Wuttig, D., Kuner, R., and Sultmann, H. (2010). Serum microRNAs as non-invasive biomarkers for cancer. *Mol Cancer.* 9:306.

9. Huang, Z., Huang, D., Ni, S., Peng, Z., Sheng, W., and Du, X. (2010). Plasma microRNAs are promising novel biomarkers for early detection of colorectal cancer. *Int J Cancer.* 127(1):118-26.

10. http://www.docstoc.com/docs/10956998/The-NIH-Roadmap-to-Understanding-Biological-Pathways-and-Networks-with-Metabolomics 11. Kuo, K.-T. T., Guan, B., Feng, Y., Mao, T.-L. L., Chen, X., Jinawath, N., Wang, Y., Kurman, R. J., Shih, I.-M. e. M., and Wang, T.-L. L. (2009). Analysis of DNA copy number alterations in ovarian serous tumors identifies new molecular genetic changes in low-grade and high-grade carcinomas. *Cancer Res.* 69(12):5267.

12. S Saldanha, A. J. (2004). Java treeview: extensible visualization of microarray data. *Bioinformatics.* 20(17): 3246-8.

13. Shannon, P., Markiel, A., Ozier, 0., Baliga, N. S., Wang, J. T., Ramage, D., Amin, N., Schwikowski, B., and Ideker, T. (2003). Cytoscape: A software environment for integrated models of biomolecular interaction networks. *Genome Res.* 13(11):2498-504.

14. Skinner, M. E., Uzilov, A. V., Stein, L. D., Mungall, C. J., and Holmes, I. H. (2009). JBrowse: A next-generation genome browser. *Genome Res.* 19(9):1630-8.

15. Barrett, T., Suzek, T. 0., Troup, D. B., Wilhite, S. E., Ngau, W.-C. C., Ledoux, P., Rudnev, D., Lash, A. E., Fujibuchi, W., and Edgar, R. (2005). NCBI GEO: mining millions of expression profiles—database and tools. *Nucleic Acids Res.* 33, D562-D566.

16. Parkinson, H., Sarkans, U., Shojatalab, M., Abeygunawardena, N., Contrino, S., Coulson, R., Fame, A., Lara, G.

G., Holloway, E., Kapushesky, M., Lilja, P., Mukherjee, G., Oezcimen, A., Rayner, T., Rocca-Serra, P., Sharma, A., Sansone, S., and Brazma, A. (2005). ArrayExpress—a public repository for microarray gene expression data at the EBI. *Nucleic Acids Res.* 33, D553-D555.

17. Irizarry, R. A., Bolstad, B. M., Collin, F., Cope, L. M., Hobbs, B., and Speed, T. P. (2003). Summaries of affymetrix GeneChip probe level data. *Nucleic Acids Res.* 31(4):e15.

18. Bolstad, B. M., Irizarry, R. A., Astrand, M., and Speed, T. P. (2003). A comparison of normalization methods for high density oligonucleotide array data based on variance and bias. *Bioinformatics.* 19(2):185-193.

19. Wright, G. W., and Simon, R. M. (2003). A random variance model for detection of differential gene expression in small microarray experiments. *Bioinformatics.* 19: 2448-55

20. Iorio, M. V., Visone, R., Di Leva, G., Donati, V., Petrocca, F., Casalini, P., Taccioli, C., Volinia, S., Liu, C. G., Alder, H., Calin, G. A., Ménard, S., and Croce, C. M. (2007). MicroRNA signatures in human ovarian cancer. *Cancer Res.* 67:8699-8707

21. Livak, K. J., and Schmittgen, T. D. (2001). Analysis of relative gene expression data using real-time quantitative PCR and the 2(-Delta delta C(T)) method. *Methods.* 25(4): 402-8.

22. Schmittgen, T. D., Lee, E. J. J., Jiang, J., Sarkar, A., Yang, L., Elton, T. S., and Chen, C. (2008). Real-time PCR quantification of precursor and mature microRNA. *Methods.* 44(1):31-8.

23. Kozomara, A., and Griffiths-Jones, S. (2011). miRBase: integrating microRNA annotation and deep-sequencing data. *Nucleic Acids Res.* D152-7

24. Pedrioli, P. G. A., Eng, J. K., Hubley, R., Vogelzang, M., Deutsch, E. W., Raught, B., Pratt, B., Nilsson, E., Angeletti, R. H., Apweiler, R., Cheung, K., Costello, C. E., Hermjakob, H., Huang, S., Julian, R. K., Kapp, E., McComb, M. E., Oliver, S. G., Omenn, G., Paton, N. W., Simpson, R., Smith, R., Taylor, C. F., Zhu, W., and Aebersold, R. (2004). A common open representation of mass spectrometry data and its application to proteomics research. *Nat Biotech.* 22:1459-1466

25. Li, C. and Wong, W. H. (2003). DNA-Chip Analyzer (dChip). In The analysis of gene expression data: methods and software. Edited by G Parmigiani, E S Garrett, R Irizarry and S L Zeger. Springer, N.Y. 120-141.

26. Yuanjian Feng, Guoqiang Yu, Tian-Li Wang, Ie-Ming Shih, and Yue Wang (2010). Analyzing DNA copy number changes using fused margin regression. *Intl J of Functional Informatics and Personalized Medicine.* vol. 3, no. 1, pp. 3-15.

27. Loi, S., Haibe-Kains, B., Desmedt, C., Wirapati, P., Lallemand, F., Tutt, A. M., Gillet, C., Ellis, P., Ryder, K., Reid, J. F., Daidone, M. G., Pierotti, M. A., Berns, E. M. M., Jansen, M. P. P., Foekens, J. A., Delorenzi, M., Bontempi, G., Piccart, M. J., and Sotiriou, C. (2008). Predicting prognosis using molecular profiling in estrogen receptor-positive breast cancer treated with tamoxifen. *BMC Genomics.* 9:239.

28. Sotiriou, C., Wirapati, P., Loi, S., Harris, A., Fox, S., Smeds, J., Nordgren, H., Farmer, P., Praz, V., Haibe-Kains, B., Desmedt, C., Larsimont, D., Cardoso, F., Peterse, H., Nuyten, D., Buyse, M., Van de Vijver, M. J., Bergh, J., Piccart, M., and Delorenzi, M. (2006). Gene expression profiling in breast cancer: understanding the molecular basis of histologic grade to improve prognosis. *J Natl Cancer Inst.* 98(4):262-72.

29. Raychaudhuri, S., Stuart, J. M., and Altman, R. B. (2000). Principal components analysis to summarize microarray experiments: application to sporulation time series. *Pac Symp Biocomput.* 455-66.

30. Golay J, Loffarelli L, Luppi M, Castellano M and Introna M (1994). The human A-myb protein is a strong activator of transcription. *Oncogene.* 9(9):2469-79.

31. Kaplan, E. L., and Meier, P. (1958). Nonparametric estimation from incomplete observations. *J Amer Statist Assn.* 53:457-481

32. Szklarczyk, D., Franceschini, A., Kuhn, M., Simonovic, M., Roth, A., Minguez, P., Doerks, T., Stark, M., Muller, J., Bork, P., Jensen, L. J., and von Mering, C. (2011). The STRING database in 2011: functional interaction networks of proteins, globally integrated and scored. *Nucleic Acids Res.* 39:D561-8.

33. Rebhan, M., Chalifa-Caspi, V., Prilusky, J., and Lancet, D. (1997). GeneCards: integrating information about genes, proteins and diseases. *Trends Genet.* 13(4):163.

34. Wu C H, Huang H, Arminski L, Castro-Alvear J, Chen Y, Hu Z Z, Ledley R S, Lewis K C, Mewes H W, Orcutt B C, Suzek B E, Tsugita A, Vinayaka C R, Yeh L S, Zhang J, and Barker WC (2002). The Protein Information Resource: an integrated public resource of functional annotation of proteins. *Nucleic Acids Res.* 30(1):35-7.

35. Online Mendelian Inheritance in Man, OMIM (TM). McKusick-Nathans Institute of Genetic Medicine, Johns Hopkins University (Baltimore, MD) and National Center for Biotechnology Information, National Library of Medicine (Bethesda, Md.). http://www.ncbi.nlm.nih.gov/omim/

36. Sherry, S. T., Ward, M. H., Kholodov, M., Baker, J., Phan, L., Smigielski, E. M., and Sirotkin, K. (2001). dbSNP: the NCBI database of genetic variation. *Nucleic Acids Res.* 29(1):308-11.

37. Sircoulomb, F., Bekhouche, I., Finetti, P., Adelaide, J., Hamida, A. B., Bonansea, J., Raynaud, S., Innocenti, C., Charafe-Jauffret, E., Tarpin, C., Ayed, F. B., Viens, P., Jacquemier, J., Bertucci, F., Birnbaum, D., and Chaffanet, M. (2010). Genome profiling of ERBB2-amplified breast cancers. *BMC Cancer.* 10:539.

38. Chuang, H.-Y. Y., Lee, E., Liu, Y.-T. T., Lee, D., and Ideker, T. (2007). Network-based classification of breast cancer metastasis. *Mol Syst Biol.* 3:140.

39. Reymond, M. A. and Schlegel, W. (2007): Proteomics in cancer. *Adv Clin Chem.* 44:103-142.

40. Chin, L., and Gray, J. W. (2008). Translating insights from the cancer genome into clinical practice. *Nature.* 452:553-563.

41. Roukos D H (2010). Systems medicine: a real approach for future personalized oncology? *Pharmacogenomics.* 11(3):283-287

42. Madhavan, S., Zenklusen, J.-C., Kotliarov, Y., Sahni, H., Fine, H. A., and Buetow, K. (2009). Rembrandt: Helping personalized medicine become a reality through integrative translational research. *Mol Cancer Res.* 7(2):157-167.

43. Weston, A. D., and Hood, L. (2004). Systems biology, proteomics, and the future of health care: toward predictive, preventative, and personalized medicine. *J Proteome Res.* 3(2):179-196.

44. Auffray, C., Chen, Z., and Hood, L. (2009). Systems medicine: the future of medical genomics and healthcare. *Genome Med.* 1(1):2.

45. Rhodes, D. R., Yu, J., Shanker, K., Deshpande, N., Varambally, R., Ghosh, D., Barrette, T., Pandey, A., and Chinnaiyan, A. M. (2004). ONCOMINE: a cancer microarray database and integrated data-mining platform. *Neoplasia.* 6(1):1-6

46. Sherlock, G., Hernandez-Boussard, T., Kasarskis, A., Binkley, G., Matese, J. C., Dwight, S. S., Kaloper, M., Weng, S., Jin, H., Ball, C. A., Eisen, M. B., Spellman, P. T., Brown, P. O., Botstein, D., and Cherry, J. M. (2001). The stanford microarray database. *Nucleic Acids Res.* 29(1):152-5.

47. Madhavan S, Sander A, Chou W-Y, Shuster A, Boone K, Dente M, Shad A and Hesse B (2011). Pediatric Palliative Care in the Age of eHealth: Opportunities for Advances in HIT to Improve Patient-Centered Communication. *Am J Prev Medicine.* 40 (5) Supplement 2: S208-S216.

SUMMARY OF THE INVENTION

It will be apparent from the above that a need exists in the art to integrate, redistribute and analyze information from disparate sources, both within and across functional domains.

It is therefore an object of the invention to provide a computer-implemented system and method for providing such integration, redistribution and renormalization.

It is another object of the invention to provide such a system and method in which information from disparate sources is normalized to allow for storage and searching.

It is yet another object of the invention to provide such capabilities over a wide area, e.g., over the Internet.

To achieve the above and other objects, the present invention is directed to a platform (e.g., Web-based) that enables basic and clinical research activities by integrating patient characteristics and clinical outcome data with a variety of high-throughput research data in a unified environment. While several rich data repositories for high dimensional research data exist in the public domain, most focus on a single data type and do not support integration across multiple technologies. The present invention in at least one embodiment includes a broad collection of bioinformatics and systems biology tools for analysis and visualization of four major "omics" types: DNA, mRNA, microRNA, and metabolites. The present invention helps facilitate systems medicine by providing easy identification of trends and patterns in integrated datasets and hence facilitate the use of better targeted therapies for cancer.

To enable the practice of an integrative translational and systems-based approach to research and medicine, the present invention allows for the development of a feature-rich, novel, and shareable research infrastructure to allow physician scientists and translational researchers to mine and analyze a variety of "omics" data in the context of consistently defined clinical outcomes data for cancer patients. By providing a powerful but easy to use interface, the present invention addresses the activation barrier for use of biomedical informatics tools by basic, clinical, and translational researchers. The present invention in at least one embodiment contains a wide variety of analytic tools and capabilities, including integrated viewers for genomic features and three-dimensional drug-target complex structures. To help support effective patient group comparisons, the present invention supports flexible clinical criteria browsing to enable selection of specific patient cohorts and facilitates the generation of detailed reports and informative publication-quality plots. Internal chemical compound libraries can be screened easily using the integrated structure and detailed molecular property search functions, with the goal of identifying new therapeutic candidate molecules. The present invention also allows researchers to securely share knowledge with others through a powerful suite of collaboration-enabling features operating within its secure environment.

The present invention provides a broad range of data reduction, visualization, and analysis tools and a large knowledge base of published "omics" datasets from previously published cancer clinical studies and a smaller set of private data sets. In at least one embodiment, four types of "omics" data are supported: mRNA and miRNA expression, copy number variation, and metabolite mass spectrometry data. All are linked to de-identified patient clinical information, markedly increasing their value. The present invention can also contain a manually curated database of small molecules as potential drug candidates for key biomarkers/target proteins and a set of curated cancer findings from integrated data sets and publications. The data repository is also designed to store multiple types of metadata associated with individual samples and patients including demographic data, clinical outcome, and tumor-specific phenotype data that could be either quantitative or qualitative, and could be either categorical or continuous. The data in are uniformly processed using validated algorithms within the R-based bioinformatics toolbox [1], formatted and mapped using R scripts, and then uploaded to the central database. The data and the analysis results can be shared within a collaborative group, or a set of groups, administered by the data provider to provide controlled access to data and analysis.

Specific data analysis tools in the environment can include differential expression analysis, heatmaps and hierarchical clustering, principal components analysis (PCA), survival analysis (Kaplan-Meier), gene-disease, gene-compound, gene-protein interaction networks rendered in the Cytoscape environment, and a collection of more specialized tools such as a toolbox for Copy Number Alteration (CNA) data analysis. The latter suite of analyses includes Chromosomal Instability (CIN) index calculations for DNA segments, cytobands, and whole chromosomes based on data from CGH array and SNP array technologies. The results of "omics" data analysis are mapped onto an integrated human genome browser at the level of either the individual patients and/or cohorts of patients, each defined by clinical attributes for ease of viewing and analysis. The present invention in at least one embodiment allows researchers to combine the commonly used clinical information—personal history, physical examination, laboratory studies, radiology studies, family history, and other pertinent data—with a detailed "omics" analysis of the patient's cancer, to facilitate exploration of the clinical and molecular factors that determine disease outcome.

As known in the art, a heatmap is a graphical representation of data where the values taken by a variable in a two-dimensional table are represented as colors. Fractal maps and tree maps both often use a similar system of color-coding to represent the values taken by a variable in a hierarchy. Leland Wilkinson developed the first computer program in 1994 (SYSTAT) to produce cluster heat maps with high-resolution color graphics. Eisen et al. (Eisen, M. B., Spellman, P. T., Brown, P. O. & Botstein, D. (1998). "Cluster analysis and display of genome-wide expression patterns". Proc. Natl. Acad. Sci. USA 95 (25): 14863-14868.). That technique can be used in the present invention. Heatmaps generated from DNA microarray data reflect gene expression values in several conditions and are typically used to represent the level of expression of many genes across a number of comparable samples (e.g., cells in different states, samples from different patients) as they are obtained from DNA microarrays.

Differential expression analysis, also known as group comparison and class comparison, determines whether the average expression pattern in one group (class) of specimens differs from that in another group and, if they differ, what genes appear to be responsible for the differences. In class discovery, there are no pre-specified classes, and the goal is to discover natural groupings of specimens or genes with the property that there is some homogeneity within groups but differences between groups. The third aim of class prediction involves the development of a multivariate mathematical model that takes as input an expression profile for a specimen or gene and gives as output a prediction of the class to which the specimen or gene belongs.

PCA is used to reduce complex differentiations into simple ones, which better enables us to separate two groups based on phenotype. It is a form of "classification". For example, ideally, people who relapse and people who do not relapse will show up as two separate clusters on a PCA plot. Any molecular data type (e.g., miRNA, mRNA, metabolomics) can be used in this way.

More generally, PCA is a mathematical procedure that uses an orthogonal transformation to convert a set of observations of possibly correlated variables into a set of values of uncorrelated variables called principal components. The number of principal components is less than or equal to the number of original variables. This transformation is defined in such a way that the first principal component has as high a variance as possible (that is, accounts for as much of the variability in the data as possible), and each succeeding component in turn has the highest variance possible under the constraint that it be orthogonal to (uncorrelated with) the preceding components. Principal components are guaranteed to be independent only if the data set is jointly normally distributed. PCA is sensitive to the relative scaling of the original variables. Depending on the field of application, it is also named the discrete Karhunen-Loève transform (KLT), the Hotelling transform or proper orthogonal decomposition (POD).

PCA is the simplest of the true eigenvector-based multivariate analyses. Often, its operation can be thought of as revealing the internal structure of the data in a way which best explains the variance in the data. If a multivariate dataset is visualized as a set of coordinates in a high-dimensional data space (1 axis per variable), PCA can supply the user with a lower-dimensional picture, a "shadow" of this object when viewed from its most informative (in some sense) viewpoint. This is done by using only the first few principal components so that the dimensionality of the transformed data is reduced.

Hierarchical clustering is used as part of group comparison. In statistics, hierarchical clustering is a method of cluster analysis which seeks to build a hierarchy of clusters. Strategies for hierarchical clustering generally fall into two types:

Agglomerative: This is a "bottom up" approach: each observation starts in its own cluster, and pairs of clusters are merged as one moves up the hierarchy.

Divisive: This is a "top down" approach: all observations start in one cluster, and splits are performed recursively as one moves down the hierarchy.

In general, the merges and splits are determined in a greedy manner. The results of hierarchical clustering are usually presented in a dendrogram.

The Kaplan-Meier estimator, also known as the product limit estimator, is an estimator for estimating the survival function from life-time data. In medical research, it is often used to measure the fraction of patients living for a certain amount of time after treatment. The estimator is named after Edward L. Kaplan and Paul Meier. A plot of the Kaplan-Meier estimate of the survival function is a series of horizontal steps of declining magnitude which, when a large enough sample is taken, approaches the true survival function for that population. The value of the survival function between successive distinct sampled observations ("clicks") is assumed to be constant. In medical statistics, a typical application might involve grouping patients into categories, for instance, those with Gene A profile and those with Gene B profile. Patients with Gene B die much more quickly than those with gene A. After two years, about 80% of the Gene A patients survive, but less than half of patients with Gene B. The usage in the present invention is just as described—to see if two patient cohorts, whether defined by a clinical parameters search (e.g., ER+ vs. ER−, men vs. women) or by the differential exhibition of molecular characteristics (e.g., mRNA or miRNA expression, copy number variation), show a statistically significant difference in survival.

Gene-disease/compound/protein in Cytoscape is the relaying of information from the Cancer Gene Index publicly available data set (provided by the National Cancer Institute) through the Cytoscape browser (http://www.cytoscape.org/), which can be embedded in the interface of the present invention. This data set includes (to give a few examples only) relationships between proteins and the drugs that bind them, relationships between a drug and the disease it treats, interactions between two or more proteins, relationships between variations in genes and the disease these may cause, etc. It also allows for link-outs to permit users to go to the primary data sources to see if they believe the representation, or if they want to do other follow up. Analyses in the present invention that result in gene lists can be an entry point into the Cytoscape view.

The chromosomal instability index (CIN) can be used in the present invention to calculate the CIN index on the cytoband level, not just on the chromosome level. We also built a (heatmap-like) graphical display interface that we embedded in the browser.

Copy-number variations (CNVs), also known as copy-number alterations (CNAs)—a form of structural variation—are alterations of the DNA of a genome that results in the cell having an abnormal number of copies of one or more sections of the DNA. CNVs correspond to relatively large regions of the genome that have been deleted (fewer than the normal number) or duplicated (more than the normal number) on certain chromosomes. For example, the chromosome that normally has sections in order as A-B-C-D might instead have sections A-B-C-C-D (a duplication of "C") or A-B-D (a deletion of "C"). This variation accounts for roughly 12% of human genomic DNA and each variation may range from about one kilobase (1,000 nucleotide bases) to several megabases in size.

CNVs may either be inherited or caused by de novo mutation. CNVs can be caused by structural rearrangements of the genome such as deletions, duplications, inversions, and translocations. Low copy repeats (LCRs), which are region-specific repeat sequences, are susceptible to such genomic rearrangements resulting in CNVs. Factors such as size, orientation, percentage similarity and the distance between the copies influence the susceptibility of LCRs to genomic rearrangement. Segmental Duplications (SDs) map near ancestral duplication sites in a phenomenon called duplication shadowing which describes the observation of a ~10 fold increased probability of duplication in regions flanking duplications versus other random regions.

Copy number variation can be discovered by cytogenetic techniques such as fluorescent in situ hybridization, comparative genomic hybridization, array comparative genomic hybridization, and by virtual karyotyping with SNP arrays.

Recent advances in DNA sequencing technology have further enabled the identification of CNVs by next-generation sequencing (NGS).

CNVs can be limited to a single gene or include a contiguous set of genes. CNVs can result in having either too many or too few of the dosage-sensitive genes, which may be responsible for a substantial amount of human phenotypic variability, complex behavioral traits and disease susceptibility. Elevating the gene copy number of a particular gene can increase the expression of the protein that it encodes.

Throughout the present disclosure, the following abbreviations will be used:
CIN—Chromosomal Instability index
CNA—Copy Number Alteration
CRC—Colorectal Cancer
CSM—Common Security Module
FMR—Fused Margin Regression
G-DOC—Georgetown Database of Cancer
GEO—Gene Expression Omnibus
GI—Gastrointestinal
HIPAA—Health Insurance Portability and Accountability Act
JMS—Java Messaging Service
miRNAs—microRNAs
NCI—National Cancer Institute
NetCDF—Network Common Data Form
PCA—Principal Component Analysis
RT-qPCR—Real-time Quantitative PCR
SCR—Significant Consensus Regions
SFTP—SSH File Transfer Protocol
SMDB—Stanford Microarray Database
UPT—User Provisioning Tool
XML—eXtensible Markup Language

BRIEF DESCRIPTION OF THE DRAWINGS

A preferred embodiment of the present invention will be set forth with reference to the drawings, in which:

FIG. 12 shows an identification of two Tamoxifen-only treated patient cohorts that are ER+;

FIGS. 13A and 13B show an analysis of whether there are clear molecular signatures that are distinct between these two patient cohorts (recurrent; non-recurrent);

FIG. 15 shows an interface for linking to external data resources.

DETAILED DESCRIPTION OF THE PREFERRED EMBODIMENT

Figure 1:
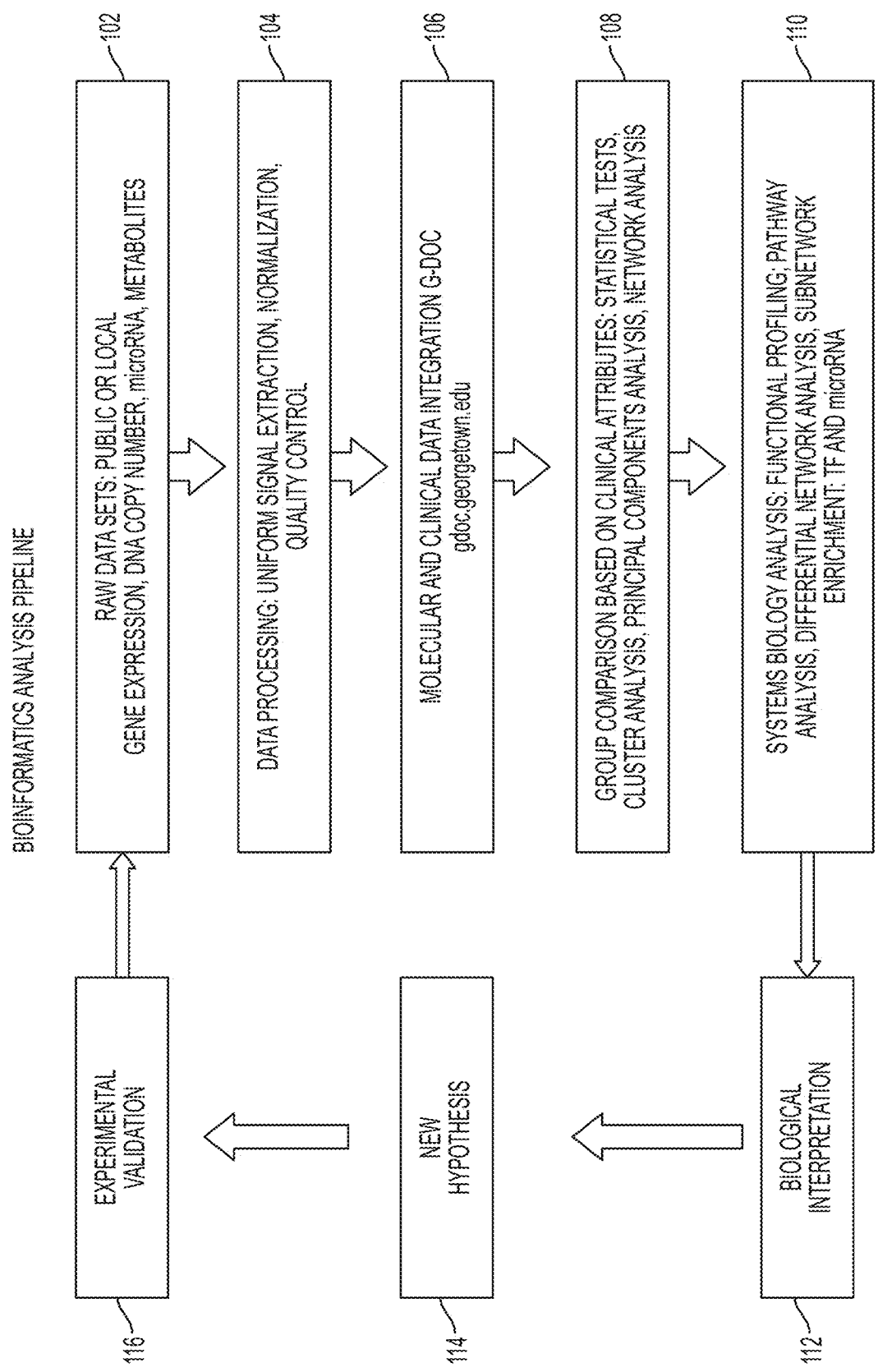
FIG. 1 shows a bioinformatics analysis pipeline according to the preferred embodiment.

A preferred embodiment of the present invention will be set forth in detail with reference to the drawings, in which like reference numerals refer to like elements or steps throughout.

The preferred embodiment has easy-to-use search capabilities for clinical data, studies, biospecimen, omics data, small molecules, and key published findings. The web portal is designed to provide powerful bioinformatics capabilities to users with a variety of backgrounds and skill levels with computational tools. FIG. 1 shows a bioinformatics analysis pipeline according to the preferred embodiment. In step 102, raw data sets are obtained from public or local sources. The raw data sets include data relating to gene expression, DNA copy number, microRNA, and metabolites. In step 104, the raw data are subjected to data processing for uniform signal extraction, normalization, and quality control. In step 106, molecular and clinical data are integrated into a single database. In step 108, a group comparison is performed based on clinical attributes; the group comparison involves statistical tests, cluster analysis, principal components analysis, and network analysis. In step 110, a systems biology analysis is performed, involving functional profiling, pathway analysis, differential network analysis, and subnetwork enrichment for TF and microRNA. In step 112, a biological interpretation is made. In step 114, a new hypothesis is formed, based on the biological interpretation. In step 116, the hypothesis is experimentally validated, and the resulting data are included in the raw data sets of step 102.

Figure 2:
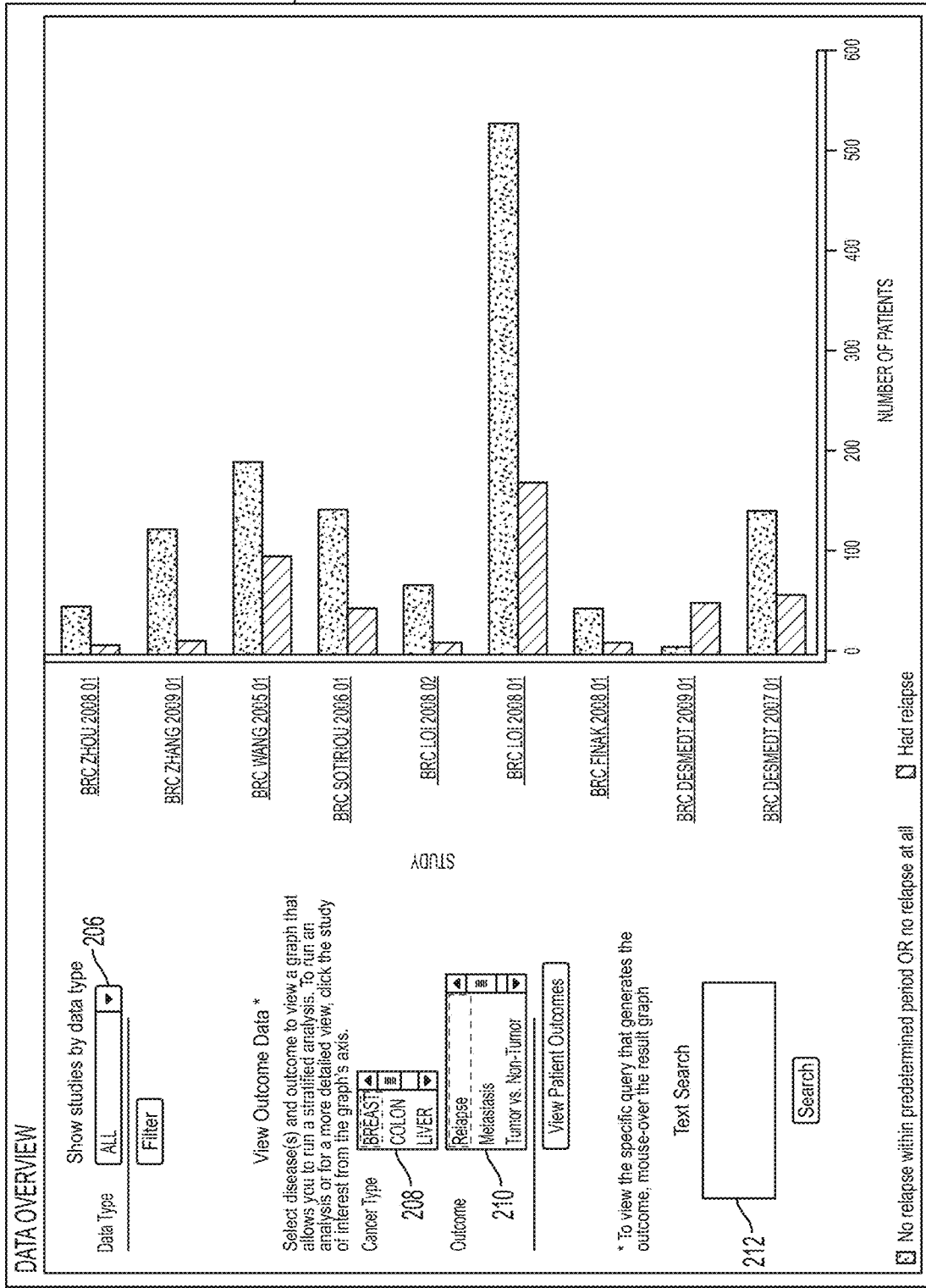
FIG. 2 shows a "Quick Start" page.

One of the most effective ways for a new user to begin is through the "Quick Start" page, shown in FIG. 2 as 200. The left-hand side 202 of this page consists of a series of selection options, and it allows users to filter the data; thus, the user can focus on only the most appropriate data sets for their needs. The right-hand side 204 of the page displays a graphical summary of the available data that fits the specified criteria. The illustrative example of FIG. 2 shows the number of breast cancer studies available in the database that have data on recurrence; a tool-tip feature helps display the various "omics" and clinical data elements available for each of these studies. Data from patient cohorts can be further analyzed from this page in a variety of ways using a right-click on the study name.

Cancer research findings can be searched by the use of a drop-down list 206 to select data type, a list 208 for cancer type, a list 210 for outcome, and a text search box 212 for receiving entries of names of genes, proteins, cancer type, investigators, or authors in the simple text box search on the home page. Findings are not meant to be comprehensive or cover all known cancer biology, but instead provide a quick search and retrieval mechanism for key discoveries in the disease areas of interest to investigators who provide data. It is anticipated that this collection will be significantly expanded over time, and may be augmented by other cancer summary data compilations.

The preferred embodiment supports compute-intensive, high-memory utilizing tasks such as class comparison, hierarchical clustering, principal component analysis, and network analysis for transcriptomic, genomic, and metabolomic data. As these data sets could be as large as 4 GB, the development of an analytic cluster to allow for several simultaneous analytic jobs was needed to support community-level use of these services. Data can also be easily used to perform advanced Systems Biology analysis of regulatory pathways and interaction networks of genes, microRNAs (miRNAs) and metabolites that are both perturbed and most relevant to the available phenotypic changes.

Figure 3A:
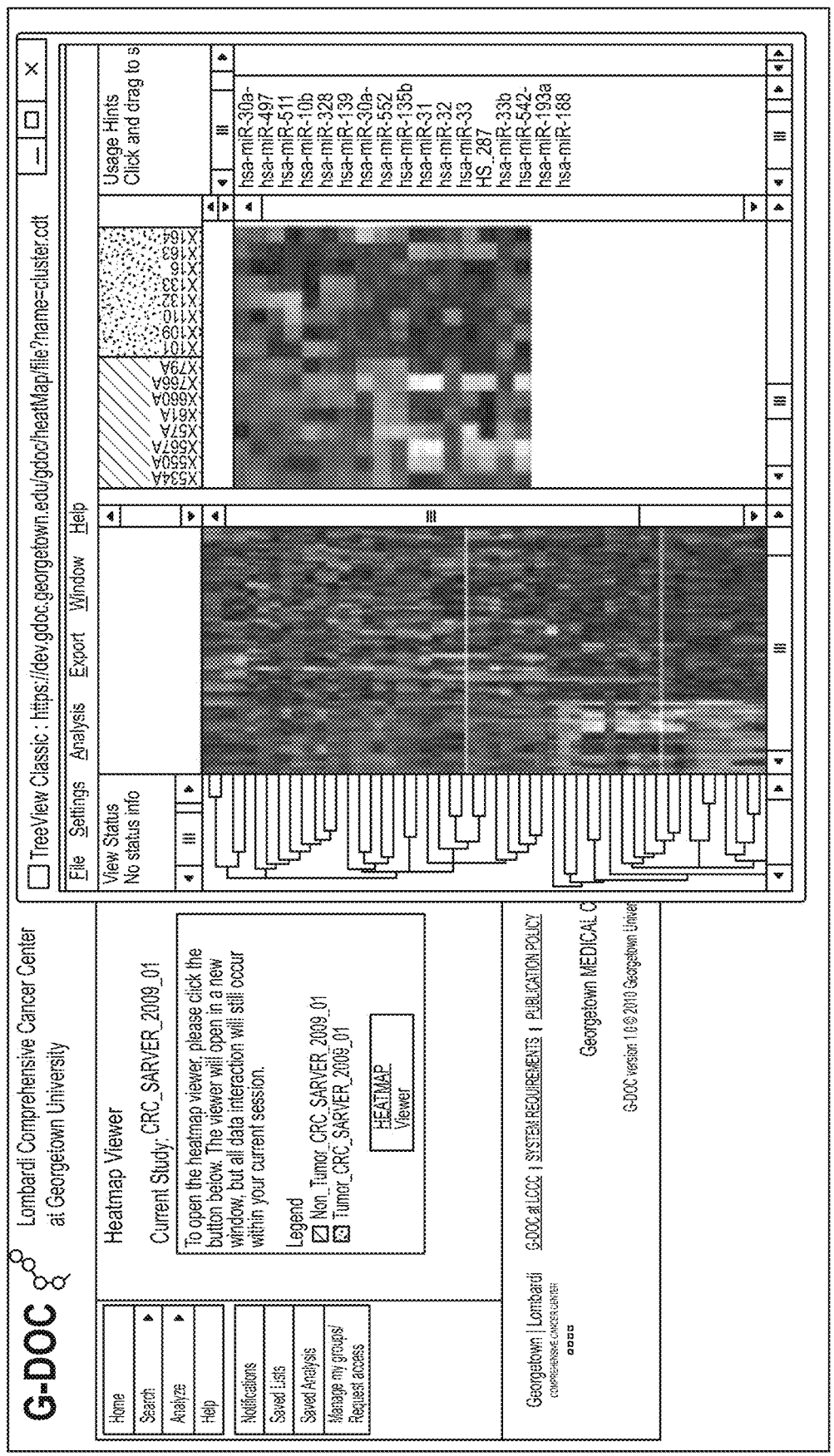
FIGS. 3A-3C show miRNAs differentially expressed between colorectal cancer and normal samples.
Figure 3B:
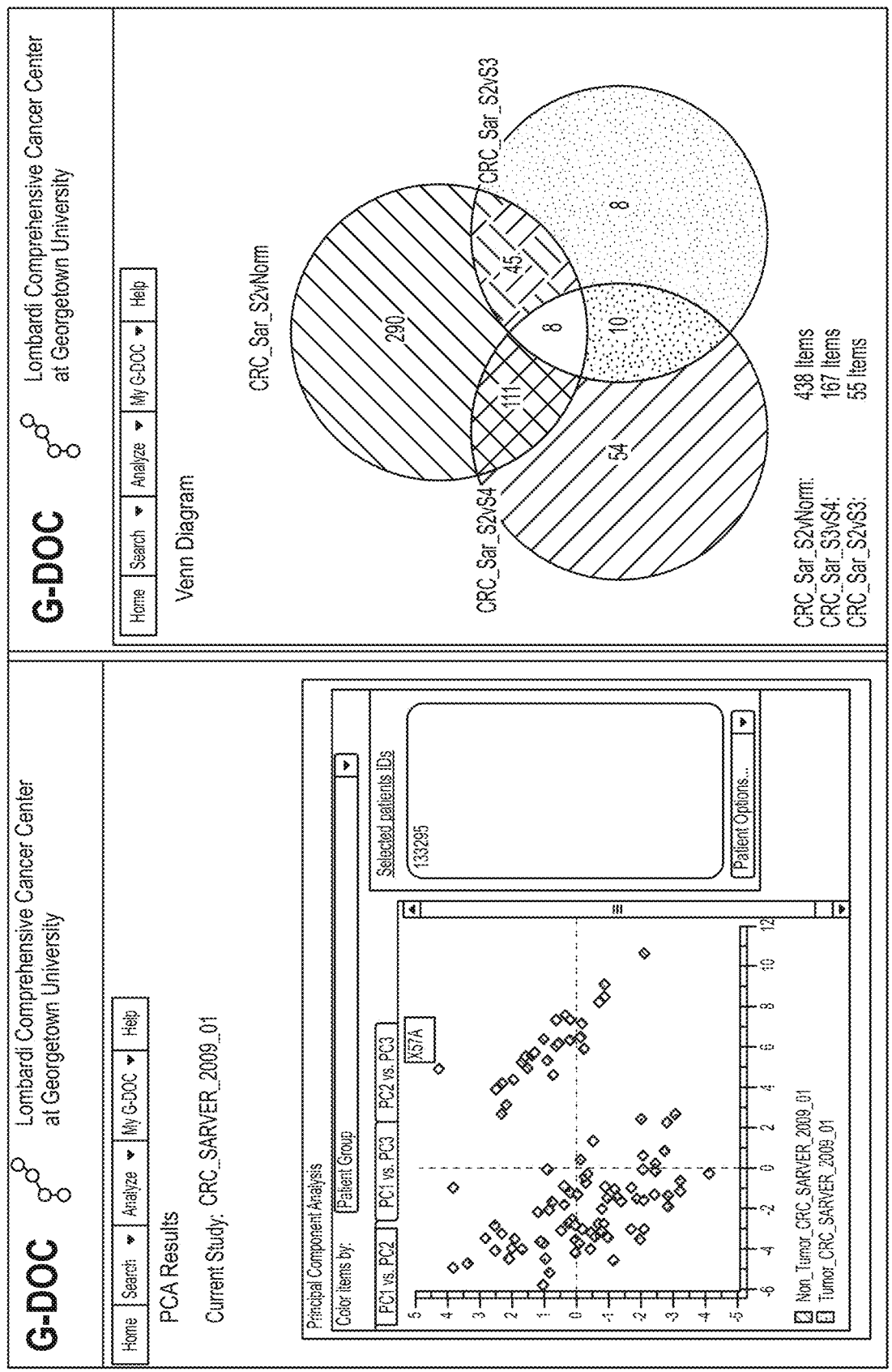
Figure 3C:
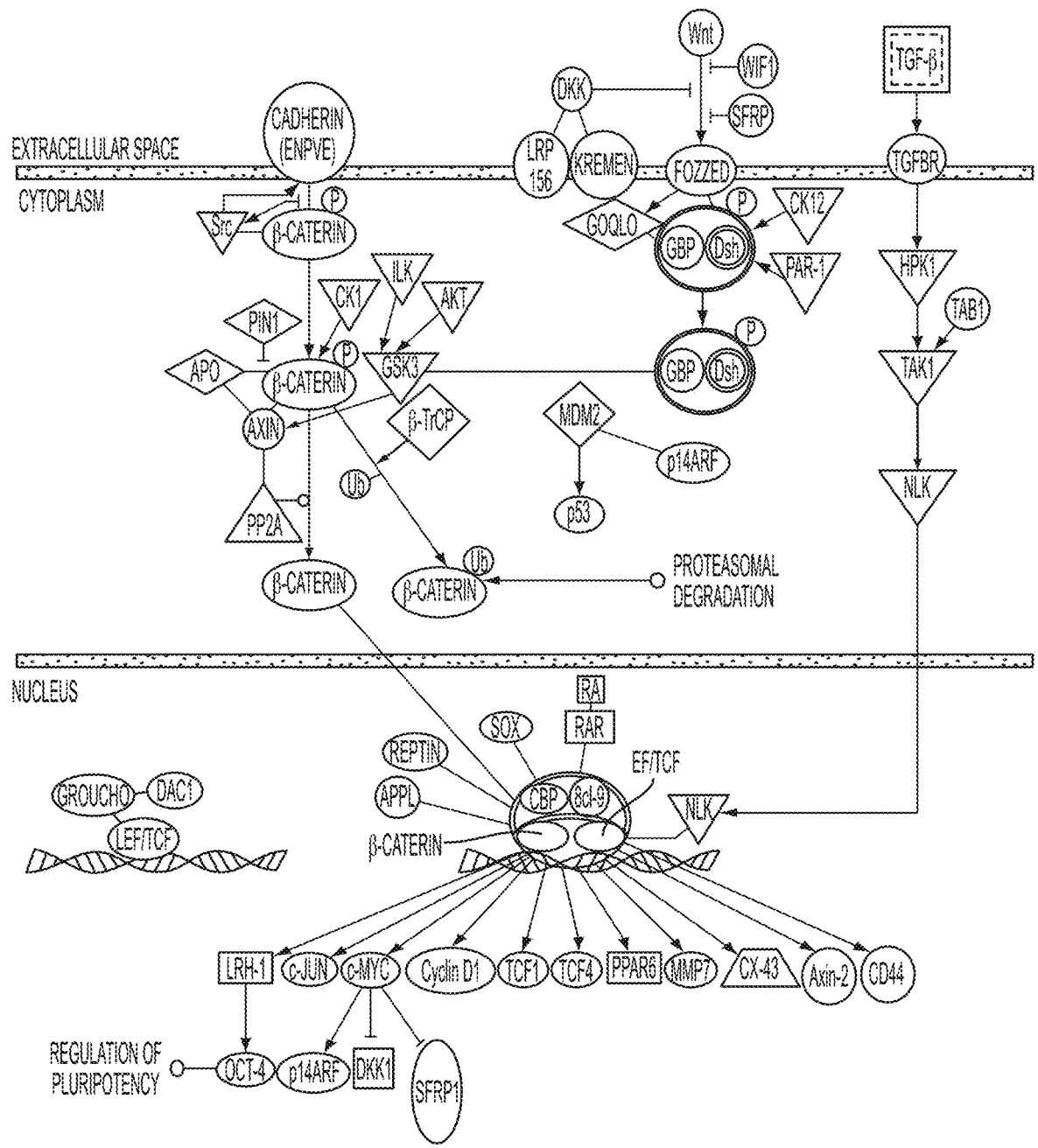

Micro RNA (miRNA) has recently emerged as a new and important class of cellular regulators. There is strong evidence that aberrant expression of miRNA is associated with a broad spectrum of human diseases including cancer, diabetes, cardiovascular and psychological disorders [2-5]. The relatively small number of miRNAs discovered in humans to date (~1733 miRNAs, miRBase17.0, [6]) are involved in regulation of a large number of human genes, perhaps as many 80% of known genes [7]. miRNAs have exceptional potential as biomarkers because of their relative abundance, highly specific expression, and stable presence in serum and plasma [8]. In fact, circulating miRNAs are sensitive biomarkers for colorectal cancer (CRC) detection, and compare favorably with the fecal occult blood test [9]. Circulating microRNAs in both urine and serum hold tremendous potential as biomarkers for both early detection of GI cancers and prognostic assessment. Processed miRNA data can be visualized using heatmaps and PCA plots to identify signatures that distinguish patient groups of interest (e.g., cancer versus normal; relapse versus non-relapse etc.). As an example, FIGS. 3A-3C show miRNAs differentially expressed between colorectal cancer and normal samples. FIG. 3A shows a heatmap viewer showing clusters of co-expressed microRNAs. FIG. 3B shows a PCA scatter plot of tumor versus normal samples based on expression data for 61 microRNA showing well separated clusters of tumors and normal samples. FIG. 3C shows a Venn Diagram showing only partial overlap between miRNAs differentially expressed in CRC stage 2, stage 3 and stage 4 with only 8 microRNAs found to be in common for all 3 sets of microRNAs. Far right: WNT signaling pathways with predicted targets of the 8 microRNA shown in grey color. Analysis of predicted targets has shown that this small group of microRNA regulates WNT signaling pathways known to be affected in colorectal cancer. A meta-analysis of differentially expressed miRNA's from stage 2, 3 and 4 CRC samples can be derived using the Venn diagram feature and then exported for further pathway analysis.

Figure 4:
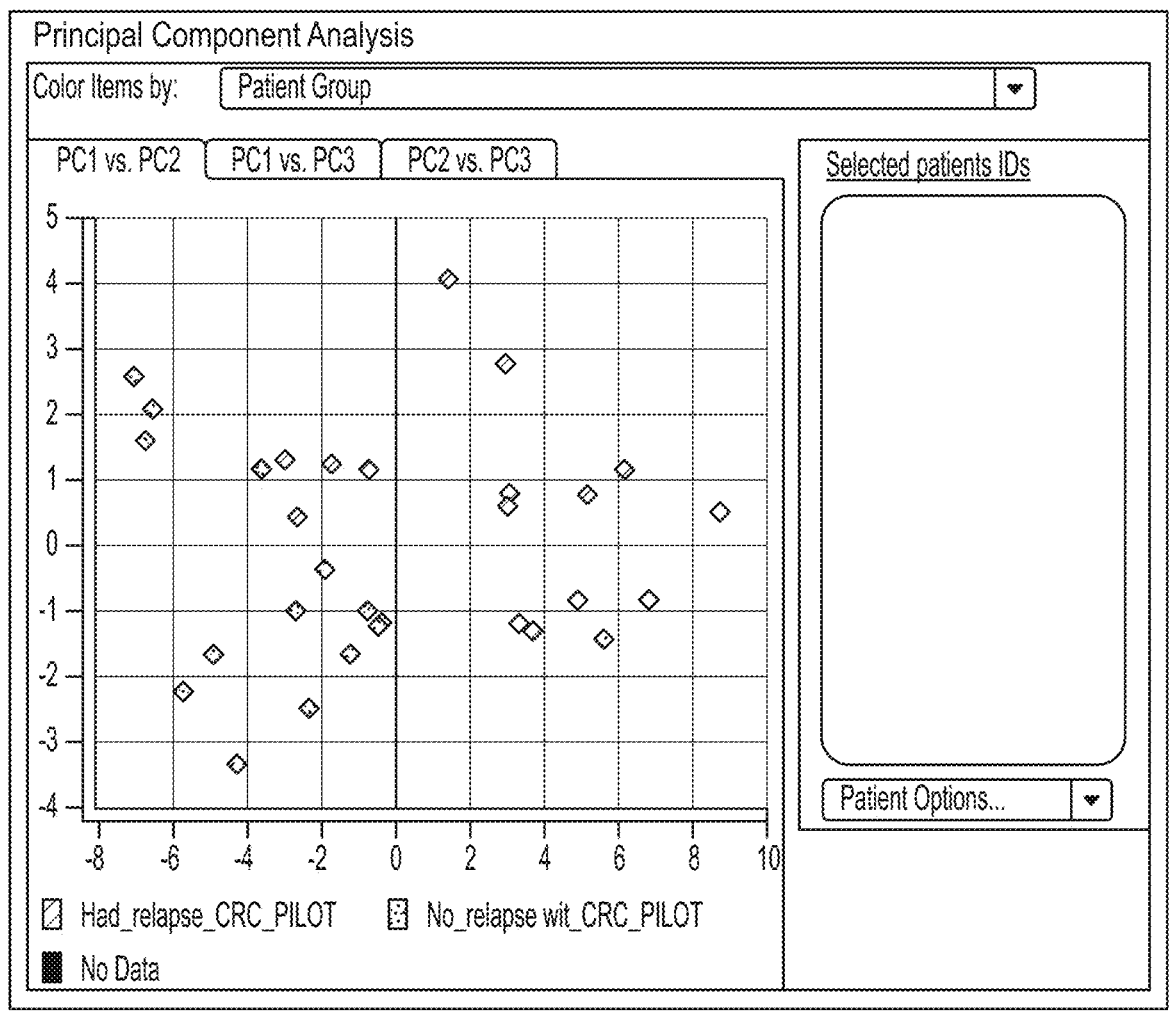
FIG. 4 shows a PCA plot using 42 metabolite peaks that differentiate between recurrent and non-recurrent cases in a gastrointestinal cancer cohort.

Metabolomics is a rapidly evolving field that aims to identify and quantify the concentration changes of all the metabolites in a given biofluid, or tissue extract, from a patient. The anticipated contribution of metabolomics to the field of biomedical science is highlighted by its presence in the current NIH Roadmap [10]. The application of metabolomics to understand the manifestation and progression of complex diseases such as GI cancers represents a powerful means to identify the earliest markers associated with attributes such as recurrence and treatment response. The preferred embodiment includes a sophisticated data analysis pipeline (see methods section) to enable detection of potential prognostic and diagnostic molecular markers in (non-invasive) serum and urine utilizing metabolomics. FIG. 4 shows a PCA plot using 42 metabolite peaks that differentiate between recurrent and non-recurrent cases in a gastrointestinal cancer cohort, fold change≥1.5; P value≤0.01. Individual samples, represented as points on the PCA plot, can be selected to view further clinical details of that specific patient.

DNA copy number changes are common in cancers, often driving underlying biology and affecting clinical outcomes. The preferred embodiment provides the genomic "map" of patient copy number profile and the significant consensus regions (SCR) derived from the Chromosome Instability (CIN) Index. The utility of this novel technique has been shown in the identification of a correlation between CIN Index and the grades of ovarian cancer subtypes [11].

Figure 5:
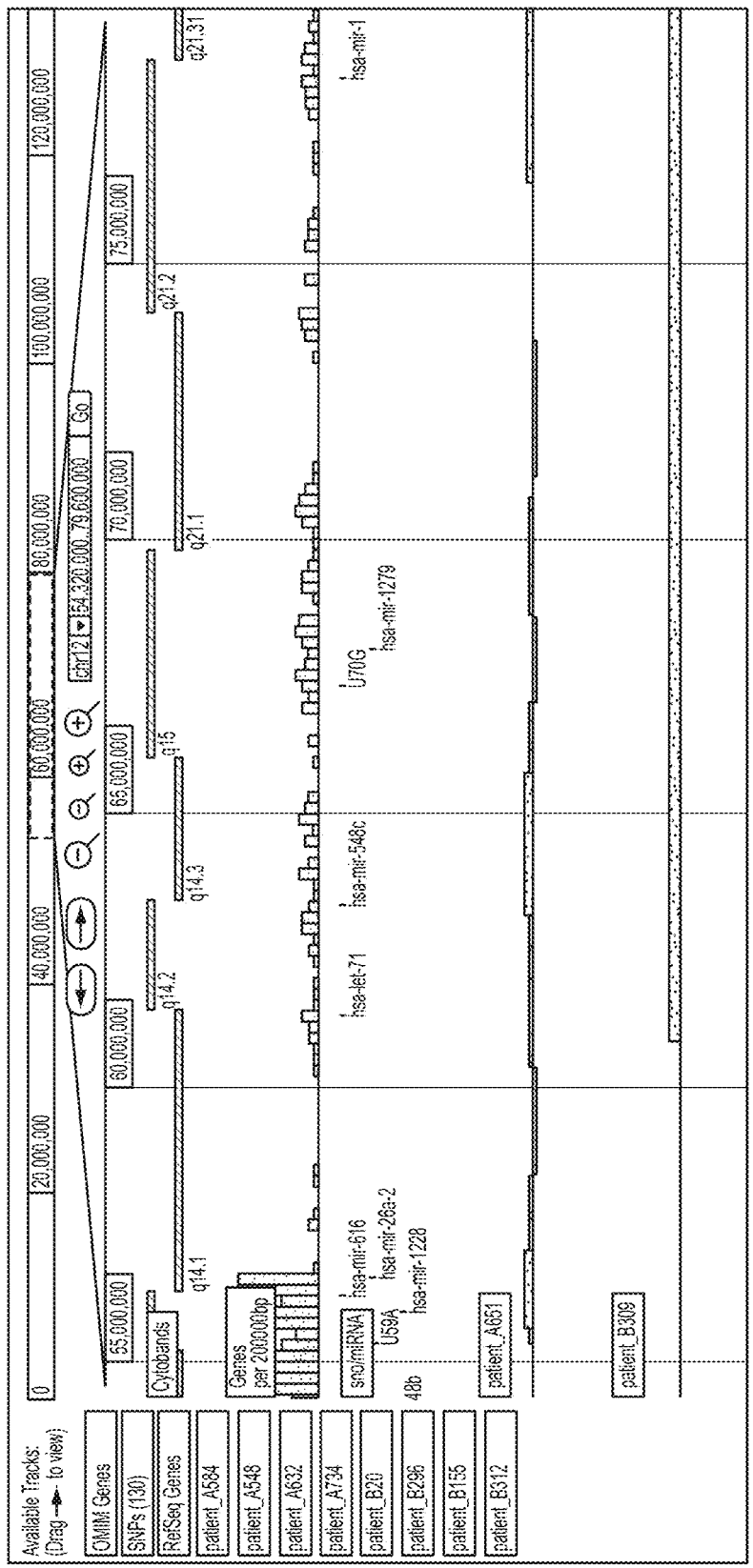
FIG. 5 shows copy number changes in a region of chromosome 12 from a pilot gastrointestinal cancer study.

Differences in a plethora of genomic features—including SNPs, miRNAs, and gene copy number—can be visualized in the genome browser by selecting the chromosomal position or by using a gene identifier. Several genomic features are available as data tiers including OMIM data and SNPs from dbSNP. FIG. 5 shows copy number changes in a region of chromosome 12 from a pilot gastrointestinal cancer study. Patient tracks can be dragged to the workspace to view genomic and clinical details. 'Omics' tracks can be dragged in to see features that map to various locations on the genome. Clear differences in copy number changes can be seen between two patients shown: a case that recurred and one that did not, viewed alongside additional genomic features such as miRNAs and SNPs in the region. Additional genomics features will be made available over time to supplement this type of view.

The preferred embodiment allows for configurable security levels for studies, and data can be made public (accessible to all users), restricted to one or more collaboration groups, or available only to the data owner, as dictated by the provider of the data. Previously published data is always made public upon loading. Collaboration groups are limited groups of users, specified by the group manager, who can share information among the members without exposing it to the entire user population. The collaboration group manager has full control over access to restricted data, and to either approve or reject requests for access. Collaboration groups allow users to share lists of patients, genes, reporters, and analysis results in a secure collaborative environment that fosters communication and team science. Additional administrative functionality includes the ability to manage user accounts and collaboration groups. The sum of these features provides a workspace for groups that are either working on a data analysis project or writing a grant as a team and can share analysis results, tools and biomarker lists within their collaboration group—all within a secure and managed environment.

The system architecture will now be described. The preferred embodiment is a web-based application that provides users with a comprehensive set of analysis routines and visualizations for a rich user experience. The application is written in Groovy on Grails, an open source development framework that runs on the Java Virtual Machine. The jQuery Javascript library is used to provide users with a cohesive and interactive interface. For more complex data visualization, the Adobe Flex framework provides users with integrated visualization components that can handle complex charts and graphs, and allow these displays to interact with other functions within the application. Besides the components developed in-house, The preferred embodiment also incorporates many third-party tools that provide data visualization capabilities. For example, Java TreeView [12] is used to display heatmaps, Cytoscape [13] to display interaction networks, and JBrowse [14] provides a genome browser with multiple annotation tracks.

The preferred embodiment is engineered and architected with future scalability as a top priority. As such, the application and architecture were designed to scale horizontally. The analysis server, web application, and database are each deployed on different virtual machines and sit behind a load balancer. As the load on the application server increases, more virtual machines can be added behind the F5 load balancer to keep up with demand.

The infrastructure consists of services and domain objects, using the common open source frameworks Spring and Hibernate (an industry-standard object relational mapping technology). The preferred embodiment has a set of RESTful services that use JSON as a transfer medium, allowing the different components to communicate in a simple manner. A third party tool, Lucene (cross-platform text search engine), is used to index the database and provide users with a global search capability.

The analysis server provides an extensible framework for analysis of study data. Analysis functionality includes the ability to perform group comparisons (t-test, Wilcoxon), and clustering (PCA and hierarchical clustering). The analysis capability is implemented using Java technologies including JMS (Java Messaging Service) and the Java Executor class library for multi-threaded processing. The analysis infrastructure is hosted on a virtual machine with 16 Gigabytes of dedicated memory. The analysis compute resources are easily scalable to larger memory or compute capacity as needed.

The preferred embodiment provides functionality to save user created lists of genes, reporters, or patients for future reference and downstream analysis. A robust set of list operations and visualizations is available including the ability to perform intersections, unions, differences, and to create and export publication-quality Venn Diagrams. User lists are persisted in the database so that they can be referenced in future sessions and shared with other users.

The security infrastructure provides for secure login as well as project and role based data access. User authorization implemented using the NCI Common Security Module (CSM) and the NCI User Provisioning Tool (UPT). All communication between the browser session and the middle-tier is encrypted using the https protocol.

The data collection is comprised of two divergent sets—public data that is available to all registrants, and private data that is supplied by, and accessible to, individual investigators and their collaboration groups. Public data sets are typically obtained from repositories such as NCBI GEO (Gene Expression Omnibus) [15] and EBI Array Express [16], while private data sets are uploaded to a secure SFTP (SSH File Transfer Protocol) server for handling by an analysis team. A set of standard operating procedures are followed before data is accepted from collaborators to ensure that all data are de-identified in accordance with HIPAA regulations; the database neither stores nor distributes patient identifiable information.

Figure 6:
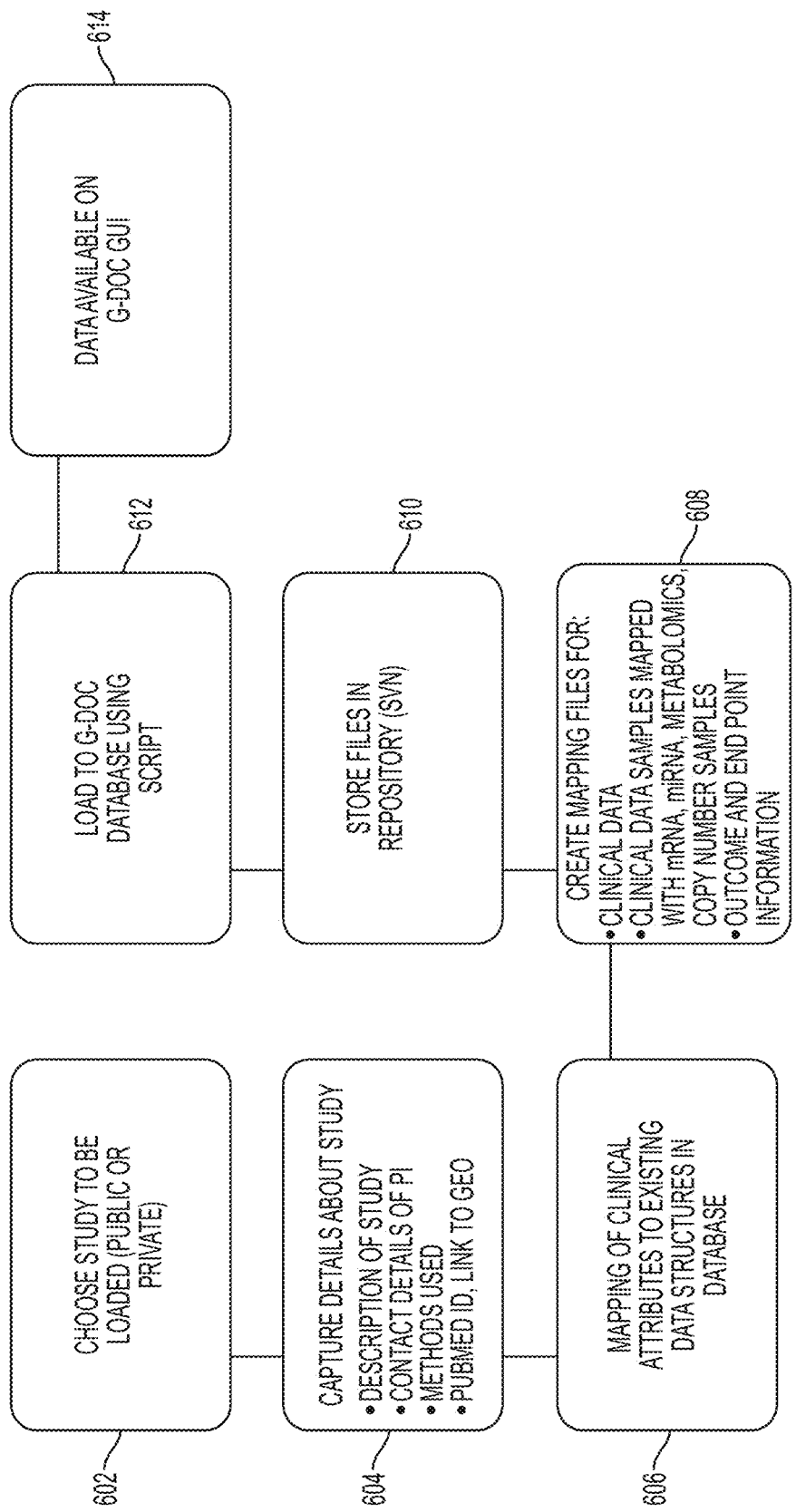
FIG. 6 shows the pre-processing of "omics" data.

Once data sets have been obtained, either from public repositories or through private transfer, the "omics" data are pre-processed and the clinical information is mapped to the existing data structures as a precursor to loading within the database. An example of this process is shown in FIG. 6. In step 602, a manager of the database chooses a study (public or private) to be loaded. In step 604, the system captures details about the study, including the description of the study, the contact details of the primary investigator, the methods used, the PubMed ID, and the link to GEO. In step 606, the clinical attributes are mapped to existing data structures in the database. In step 608, mapping files are created for clinical data, clinical data samples mapped with mRNA, miRNA, metabolomics, and copy number samples, and outcome and end point information. In step 610, the files are stored in the repository, and in step 612, the files are loaded into the database using an automated script. The loading script is written in Groovy. In step 614, the data are made available to users through the GUI.

Uniform pre-processing and normalization ensures maximum comparability between analyses and studies, and ensures that the data provides the greatest scientific leverage to the user community. Specific pipelines have been established, tailored to each data-type, and emphasize standard and uniform data pre-processing to ensure utmost quality, a key factor in minimizing noise and false positives. All data and accompanying query features are subjected to rigorous QC procedures prior to being made available in the production environment.

Several files are created describing the clinical attributes with respect to its type and vocabulary, outlining specifics such as format and range. Special files are also created for each data type in the study describing the mapping between the clinical and corresponding high-throughput data samples (after pre-processing). The summary, study characteristics, and contact information are captured in a separate format. This set of files is stored in a version controlled data repository using a consistent naming convention to describe each study: Cancer-abbreviation_Principal-investigator_Publication-year_iteration (e.g., BRC_WANG_2005_01 for Wang, et al. 2005; PMID: 15721472). Special attention is paid to capturing and persisting the disease outcomes and endpoint information, as these serve to enable a series of value-added features (e.g., Quick Start, interactive Kaplan-Meier plots) that better support translational research activities. Studies are stored in an Oracle 10g relational database, which consists of 44 common tables. For each new study loaded, a separate schema is created consisting of a set of 12 study-specific tables. All processed data files pertaining to a particular study are loaded separately onto a computation-centric server designed to handle high throughput data analysis. Analyses that are run against study data reference their respective processed (binary) file in order to complete a variety of statistical routines. All analysis routines that run in the environment are written in the R language to ensure modularity, ease of deployment, and high performance on the computational server nodes that provides analytic services to the user community.

Figure 7:
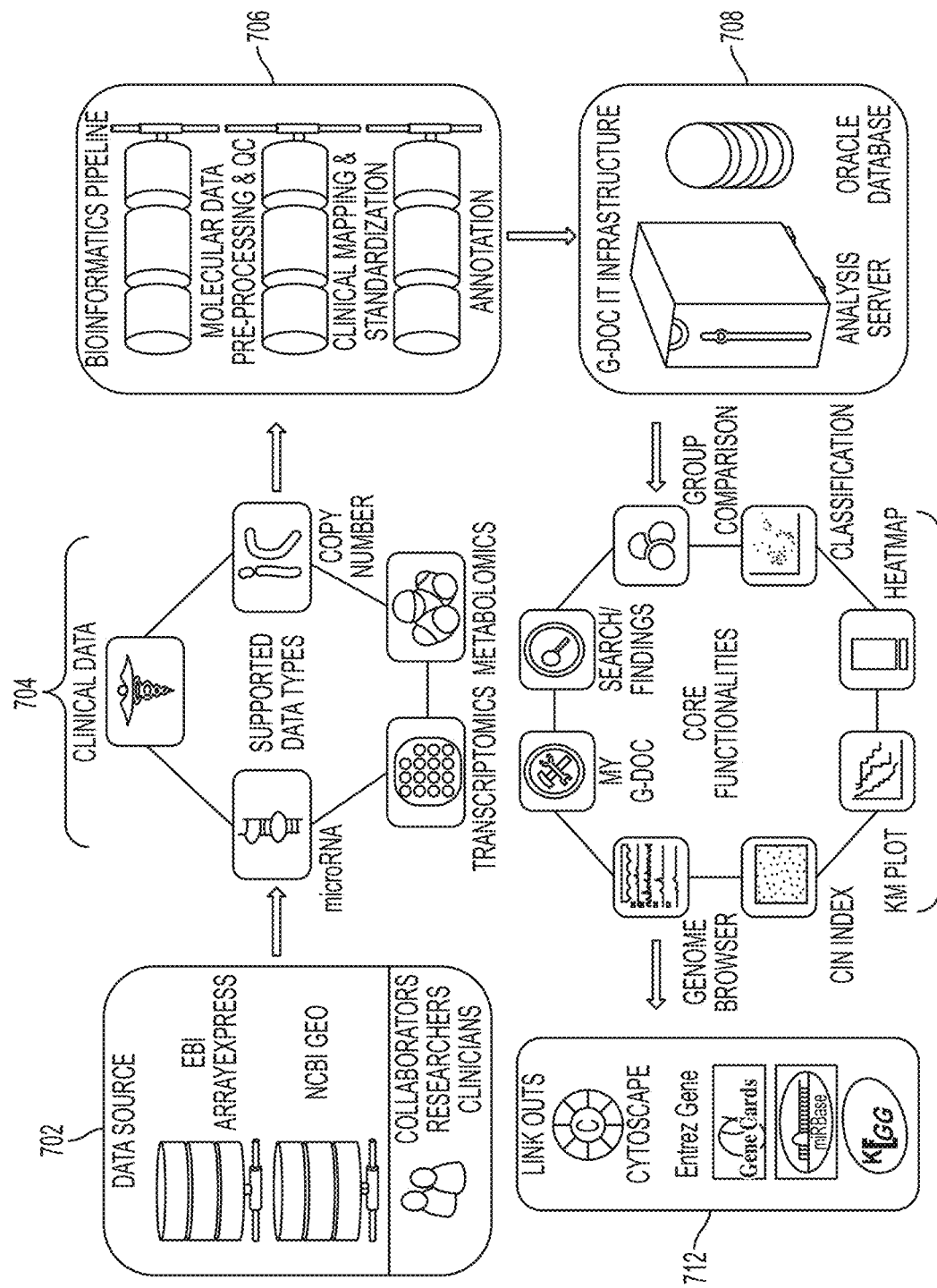
FIG. 7 shows a high-level overview of data, annotations and analysis.

A high-level overview of data, annotations and analysis available is illustrated in FIG. 7. Data from data sources 702, in supported data types 704, are received into the bioinformatics pipeline 706. The processed data are input into the IT infrastructure (hardware) 708, including an analysis server and a database. The core functionalities 710 provide an output 712.

The processing that occurs prior to data entry is detailed below for the four major types of "omics" data presently available (mRNA, miRNA, metabolomics, copy number). High-throughput sequencing information (exon sequencing, CHIP-Seq, RNA-Seq) and other related data types can be supported.

mRNA expression data: Much of the data currently are mRNA expression data produced by array hybridization experiments, including both two channel ratio data and single-channel intensity data. These are retrieved in a raw .CEL file format (Affymetrix) or a tab delimited text file format (Agilent), as appropriate, from the public archives or from the lab which generated this data. Other formats are being considered for future versions of the tool. Pre-processing of microarray data primarily involves normalization with either RMA (Robust Multichip Average) [17] or Quantile Normalization [18] followed by log transformation of the data. More information on these standard normalization strategies is available at http://www.bioconductor.org. Significant post-processing effort is expended to ensure data quality and retention of the biological information provided. Transcripts (mRNAs) are mapped on the genome in the JBrowse genome browser interface based on Build 36 of the NCBI genome.

Figure 8:
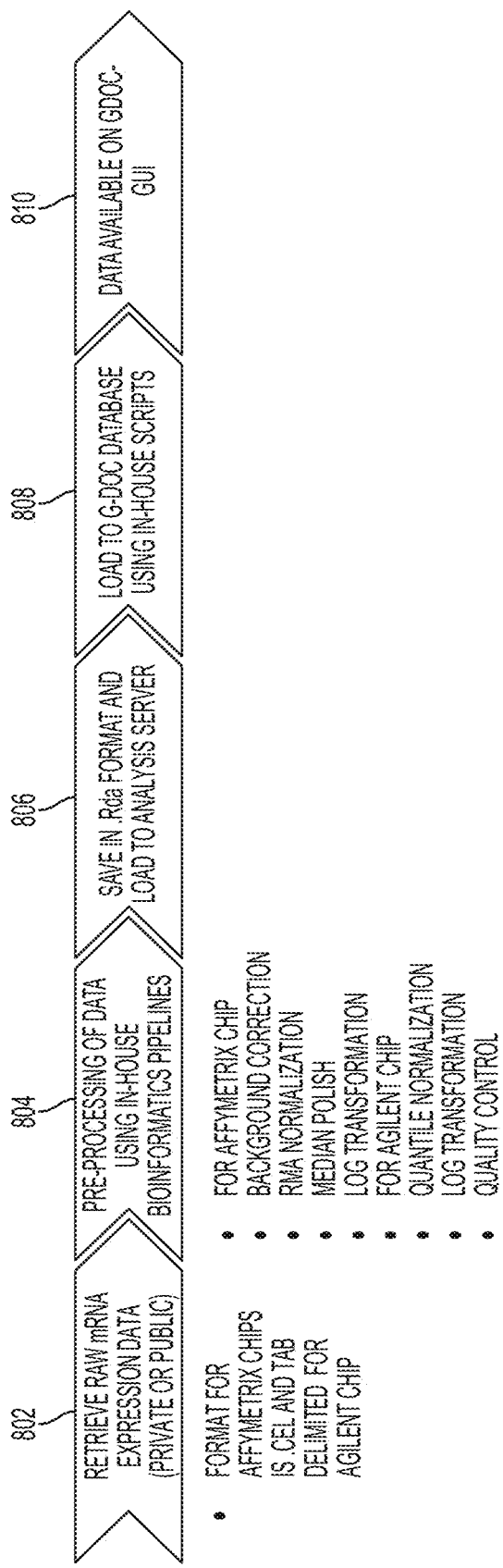
FIG. 8 shows the normalization of raw mRNA expression data.

As shown in FIG. 8, in step 802, raw mRNA expression data (public or private) are retrieved. The data format is .CEL for Affymetrix chips and tab-delimited for Agilent chips. In step 804, the data are pre-processed using bioinformatics pipelines. For data from Affymetrix chips, the pre-processing includes background correction, RMA normalization, median polish, and log transformation. For data from Agilent chips, the pre-processing includes quantile normalization and log transformation. For data from both kinds of chips, the preprocessing includes quality control. In step 806, the pre-processed data are saved in .Rda format and loaded to an analysis server. In step 808, the data are loaded to the database using scripts. In step 810, the data are made available through the GUI.

The experimental details should be provided in the IDF file format. The IDF file is used to give an overview of the experiment, including the experimental variables (factors), quality control strategy, contact details, publication information and protocols.

A mapping file is also provided, which is usually in the form of a Sample and Data Relationship (SDRF) file. This is a tab-delimited format that describes the relationships between samples, array, data, and other objects used or produced in the experiment. An SDRF contains one or more column headers for the following main types of metadata:

Name—name of the sources and/or samples used in the array. There can be multiple columns of names.

Protocol REF—provides ID(s) for one or more protocols used in the array and referenced in a corresponding IDF file.

File—one or more columns that list files produced in the investigation. Examples: Array Data File, Derived Array Data File Attribute—values, comments, or characteristics relating to and modifying one of the above kinds of columns. Examples: Date, Provider, Performer, Label, Factor Values.

The data provider should provide specific details on Affymetrix platforms used in the experiment (e.g., HG-U133A, HG-U133B, HG-U133A Plus 2, HG-U133A2). Currently, the Affymetrix, Agilent and lumina platforms are supported. Other platforms can also be supported.

The collaborator should provide the raw data files (.cel format for the platform used). The data files are uniformly processed to ensure maximum comparability.

For Affymetrix chip arrays, the preprocessing is done in the following steps. The first step is background correction. Probe-level data for each chip are background corrected independently using a probabilistic model. Non-linear correction is done on per chip basis. The second step is quantile normalization. The background corrected probe-level data on each chip are normalized to a common set of quantiles, Q, derived from background corrected data from all chips. The third step is expression calculation. This is performed separately for each probe set. The logarithmic intensities for each microarray are estimated from the linear model $\log_2(N_{ij}) = P_j I_i e_{ij}$ using median-polish, where $I_i$ is the logarithmic intensity for the $i^{th}$ microarray, $N_{ij}$ is the background corrected and normalized intensity of the $j^{th}$ PM probe of the $i^{th}$ chip, $P_j$ is the effect of the $j^{th}$ PM probe of the probe set, and $e_{ij}$ is a random error term. Further details on the RMA algorithm can be obtained from the following publication: Irizarry, R. A., et al. Exploration, Normalization, and Summaries of High density Oligonucleotide Array Probe Level Data. (2003) Biostatistics, 4, 249-264.

The following four preprocessing steps are performed on data from Agilent chips. The first is background correction, in which "normexp" is the R function used. It is a convolution of normal and exponential distributions is fitted to foreground intensities using background intensities as a covariate, and the expected signal given the observed foreground becomes the corrected intensity. The second step is normalization between arrays, in which "quantile" is the R function used. The third step is offset. The purpose of this calculation is to shrink the log ratios to zero at the lower intensities and thus to reduce the variability of log-ratios for low intensity spots. The optimum choice is 50, which is added to the intensity values before the log transformation. The fourth step is summarization. Agilent 4×44 chips contain a set of non-control probes that are replicated up to ten times. These probes are spread over the chip and allow measuring the chip reproducibility in terms of the coefficient of variation of the array. A lower CV median indicates a better reproducibility of the array. Replicated non-control probes have been collapsed into a single value computed as the median of the probes intensities belonging to the same set. Besides this other technical control/spike-in probes are also filtered leaving finally 41,000 probes/genes.

Various methods are used to check the quality of the gene expression data. Some include scatter plots, NUSE (Normalized Unscaled Standard Error) plots, etc.

miRNA expression data: MicroRNA is a subject of growing interest for the clinical, translational, and basic science cancer communities. A data pre-processing pipeline was developed for microRNA expression data that supports the major high-throughput platform formats: oligonucleotide microarrays (Agilent and Illumina) and real-time quantitative PCR (RT-qPCR) arrays (Life Technologies). Microarray-generated datasets are processed from raw data files using global median normalization [19,20], while RT-qPCR data are processed using comparative C(T) method [21] and normalized to the average signal of endogenous controls [22]. These microRNA reporter Ids are mapped to mature miRNA accession numbers in miRBase [23] and hyperlinked to on-line public databases (miRBase, Entrez and iHOP), providing instant access to comprehensive microRNA genomic and deep sequencing information as well as predicted targets. miRNAs are also mapped on the genome using the JBrowse genome browser interface.

Figure 9:
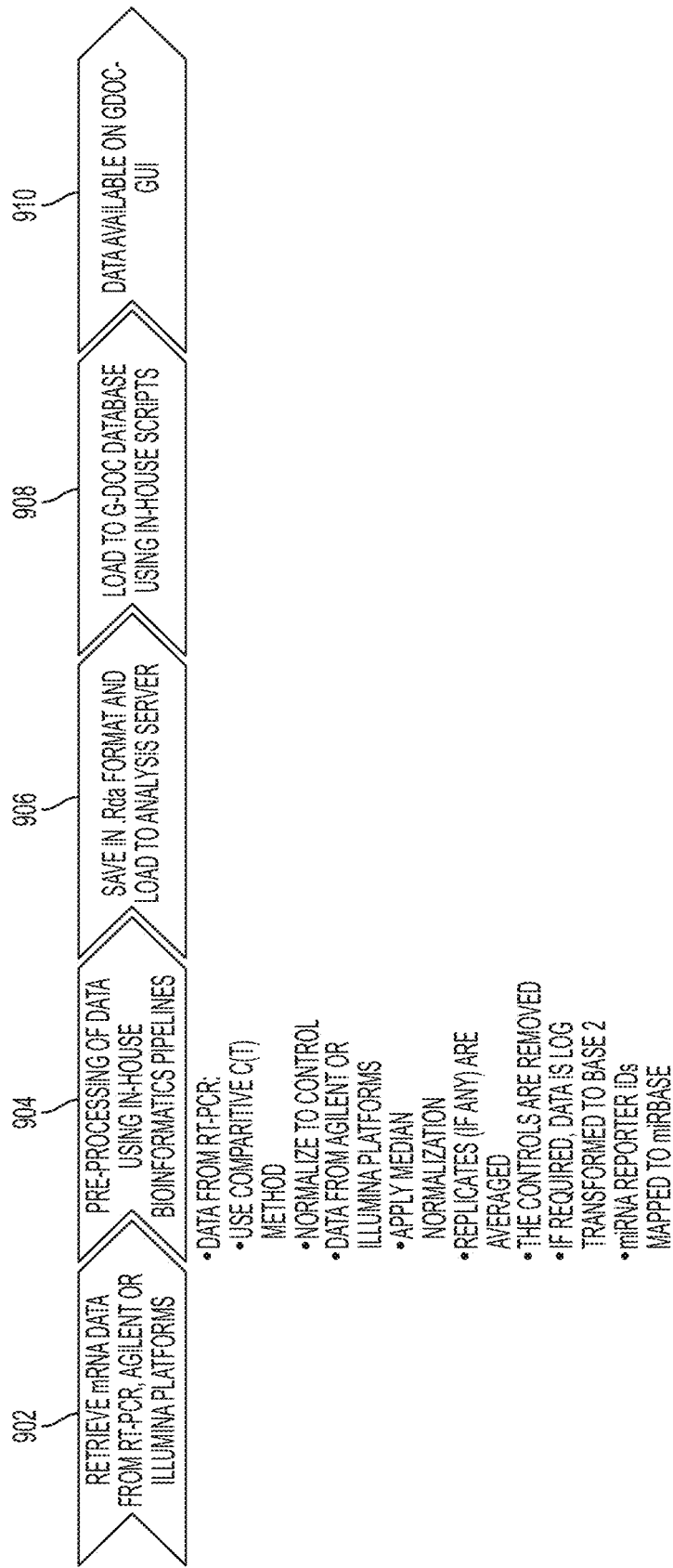
FIG. 9 shows the normalization of miRNA data.

As shown in FIG. 9, in step 902, the miRNA data are retrieved from the RT-PCR, Agilent, or Illumina platform. In step 904, the data are pre-processed using bioinformatics pipelines. For data from the RT-PCR platform, the pre-processing uses the comparative C(T) method and normalizes to control. For the data from the Agilent and Illumina platforms, the pre-processing applies median normalization. For data from any platform, replicates (if any) are averaged, the controls are removed, the data are log transformed to base 2 if required, and the miRNA reporter ID's are mapped to miRBase. In step 906, the data are saved in the .Rda format and loaded to the analysis server. In step 908, the data are loaded to the database using scripts. In step 910, the data are made available on the GUI.

The following pre-processing steps are performed. Apply median normalization. Replicates (if any) are averaged. The controls are removed. If required, data is $\log_2$ transformed.

Metabolomics data: Metabolomics is one of the newer "omics" sciences, and aims to study global profiles of small molecule metabolites within a biological system under a given set of conditions. Typically these experiments are performed on biofluids such as urine, saliva, or blood plasma but isolated cells and tissues may also be used. The metabolomics data collection is exclusively mass spectrometric data, but the data structures are sufficiently generic to support other typical metabolomics data types (e.g., NMR, gas chromatography) in the future. For mass spectrometry data, a number of vendor-specific software programs, tailored to the specifics of the acquisition hardware, are available to convert spectral data into universal data exchange formats such as NetCDF (http://http://www.unidata.ucar.edu/software/netcdf/), mzXML [24], and mzDATA. To ensure maximal future flexibility, the pre-processing pipeline is built to work with all these formats. The metabolomics data were processed into a data matrix format with samples as columns and peaks/metabolites as rows, and were normalized row-wise or column-wise in a sequential manner to minimize systematic variance and improve the performance for downstream statistical analysis.

Figure 10:
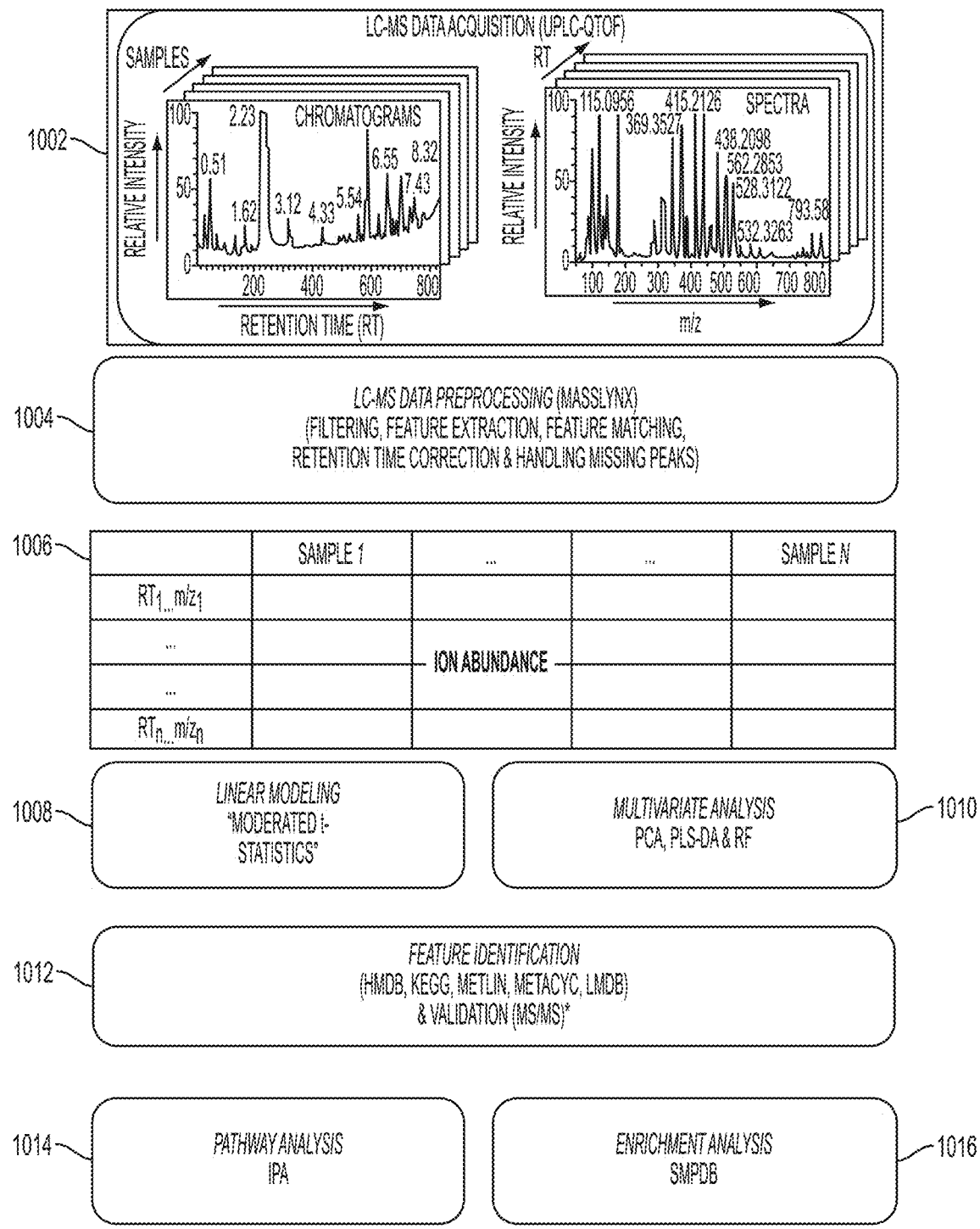
FIG. 10 shows the normalization of metabolomics data.

As shown in FIG. 10, in step 1002, LC-MS data are acquired. In step 1004, the data are preprocessed using MassLynx. The preprocessing includes filtering, feature extraction, feature matching, retention time correction, and handling of missing peaks. In step 1006, the abundance of each ion in each sample is determined. In step 1008, linear modeling is used to produce moderated t-statistics. In step 1010, multivariate analysis (PCA, PLS-DA, and RF) is performed. In step 1012, feature identification (HMDB, KEGG, METLIN, METACYC, and LMDB) and validation (MS/MS) are performed. In step 1014, pathway analysis (IPA) is performed. In step 1016, enrichment analysis (SMPDB) is performed.

In the pre-processing, replicates (if any) are averaged. Data is $\log_2$ transformed, as the system expects $\log_2$ values. This transformation automatically scales the data.

DNA copy number data: Considerable attention has been paid to understanding the gross chromosomal modification events that are common within many types of cancer. While the technologies used have progressed (e.g., SNP and cDNA array hybridization replacing LOH), significant interest remains in identifying the aberrations that occur within the development and progression of neoplasias. To ensure that the system can enable investigators to best use this type of data, a data processing pipeline was developed using R (http://www.r-project.org/) for analysis and visualization of DNA copy number data obtained from a variety of platforms. Raw data from the most common platforms, Affymetrix SNPchip and Agilent CGH arrays, are pre-processed using D-Chip [25] to extract a signal for individual probes. Piecewise constant segments of copy number profiles are estimated based on the Fused Margin Regression (FMR) method [26]. Probe-level data are further processed to calculate copy number segments and chromosomal instability index [11], one of the value-added analyses that come pre-generated. Segment data are used for calculation of CIN index at the level of whole chromosomes and individual cytobands [11].

Figure 11:
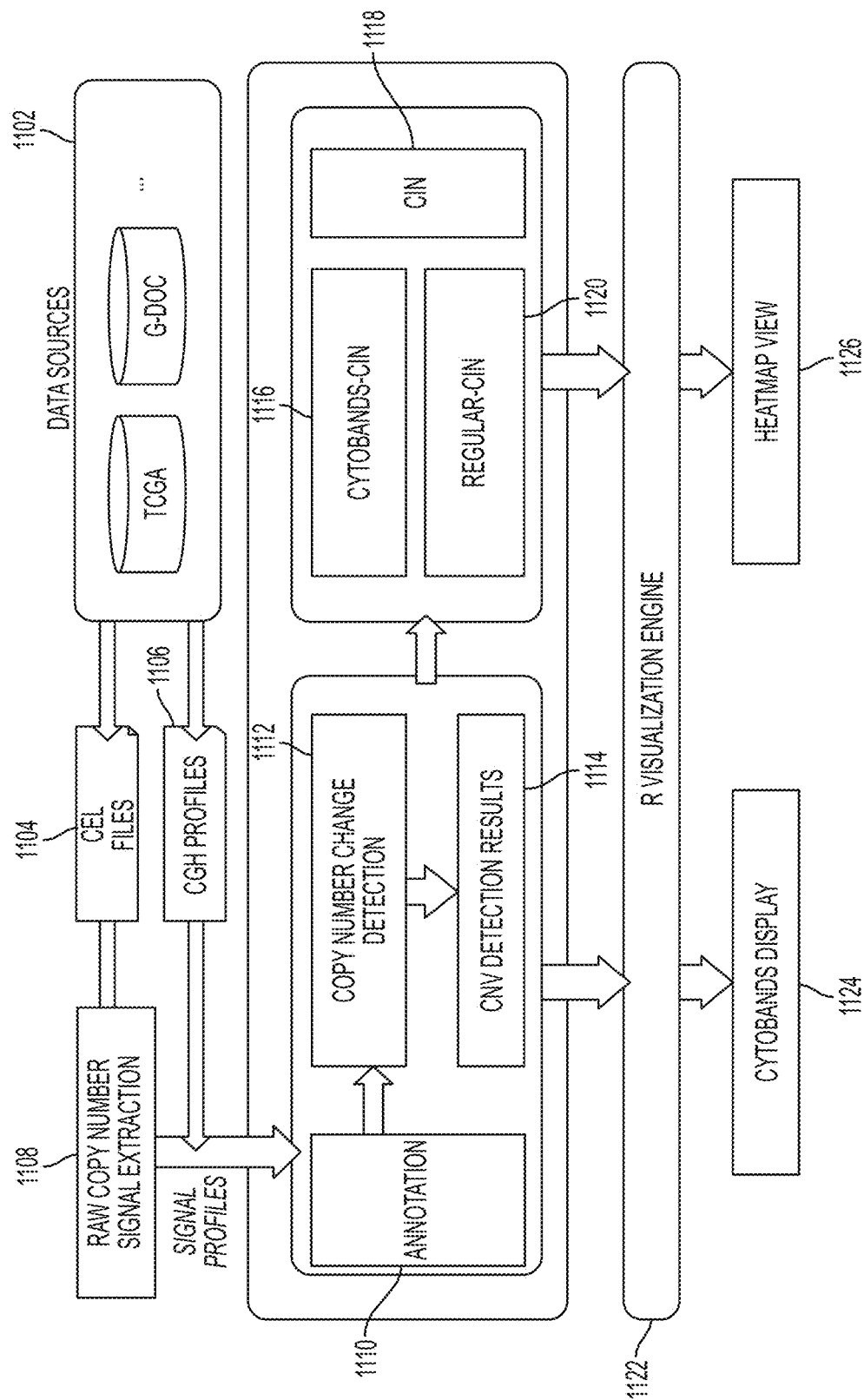
FIG. 11 shows the normalization of DNA copy number data.

As shown in FIG. 11, first, in step 1102, data are obtained from data sources. The data are organized as .CEL files in step 1104 and as CGH profiles in step 1106. In step 1108, raw copy number signals are extracted from the .CEL files to produce signal profiles. The signal profiles and the .CGH profiles are input to a process including annotation 1110, copy number change detection 1112, CNV detection 1114, cytobands-CIN 1116, CIN 1118, and regular-CIN 1120. The results of the CNV detection 1114 and the regular-CIN 1120 are supplied to an R visualization engine 1122, which produces a cytobands display 1124 and a heatmap view 1126.

These are usual pre-processing steps followed by our analysts: The raw probe intensities from the .cel files of both tumor and normal samples are extracted from the file given. The annotation file that corresponds to the platform/array used is also taken. The copy number signal is normalized by dividing the signal of tumor by that of normal. FMR (Fused margin regression) is applied to detect the change in copy number. Segments are created from the above—they are matrices wherein each row is a patient, each column is a chromosome, each cell in the matrix is a list (the segment result) that contains the following values: segment start, segment end, and copy number value.

There is a parameter in the FMR function referred to as the "sensitivity parameter", which controls the degree we handle the breakpoints. We can set a tight parameter to get more segments which can be viewed as sensitive to break points, and we can also set lax parameter to get fewer segments, since they are combined together due to the non-sensitive to break points.

The sample profiles are annotated to make sure the probes are arranged according to their position on the chromosome. A CIN index (Chromosome instability index) is calculated from the segments. The CIN index is calculated for both chromosome (denoted as "Regular CIN") and cytobands (denoted as "Cytoband CIN"). Regular CIN is a scale number for each chromosome for patients. Cytobands CIN is a scale number for each cytoband for patients. So, the CIN matrix is simply each row is a reporter(corresponding to either chromosome or Cytoband); and each column is a sample/patient. This CIN matrix is saved as an .Rdata file and displayed as a heat map.

Figure 11A:
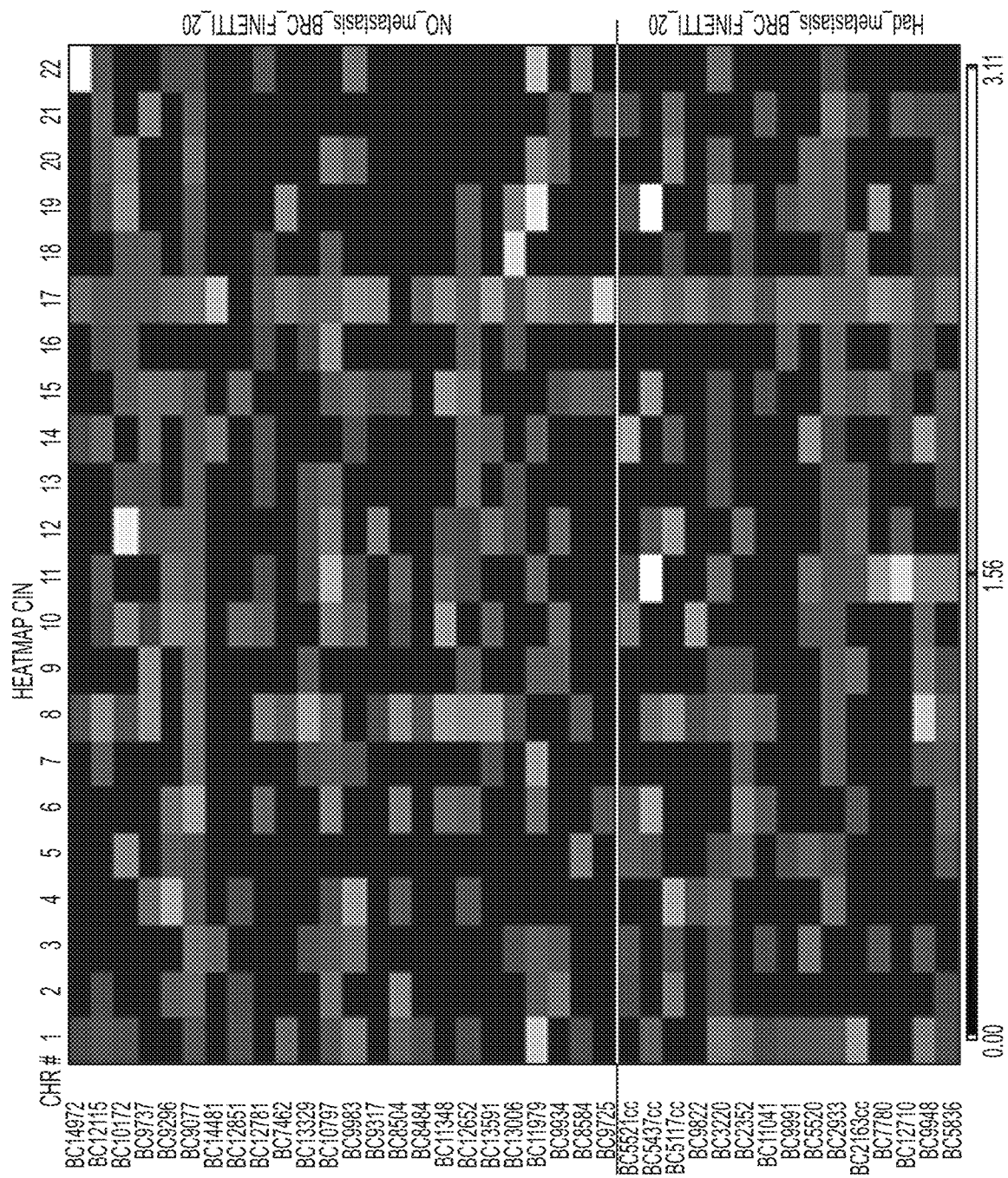
FIGS. 11A and 11B show two heatmap-type views of the copy number data.
Figure 11B:
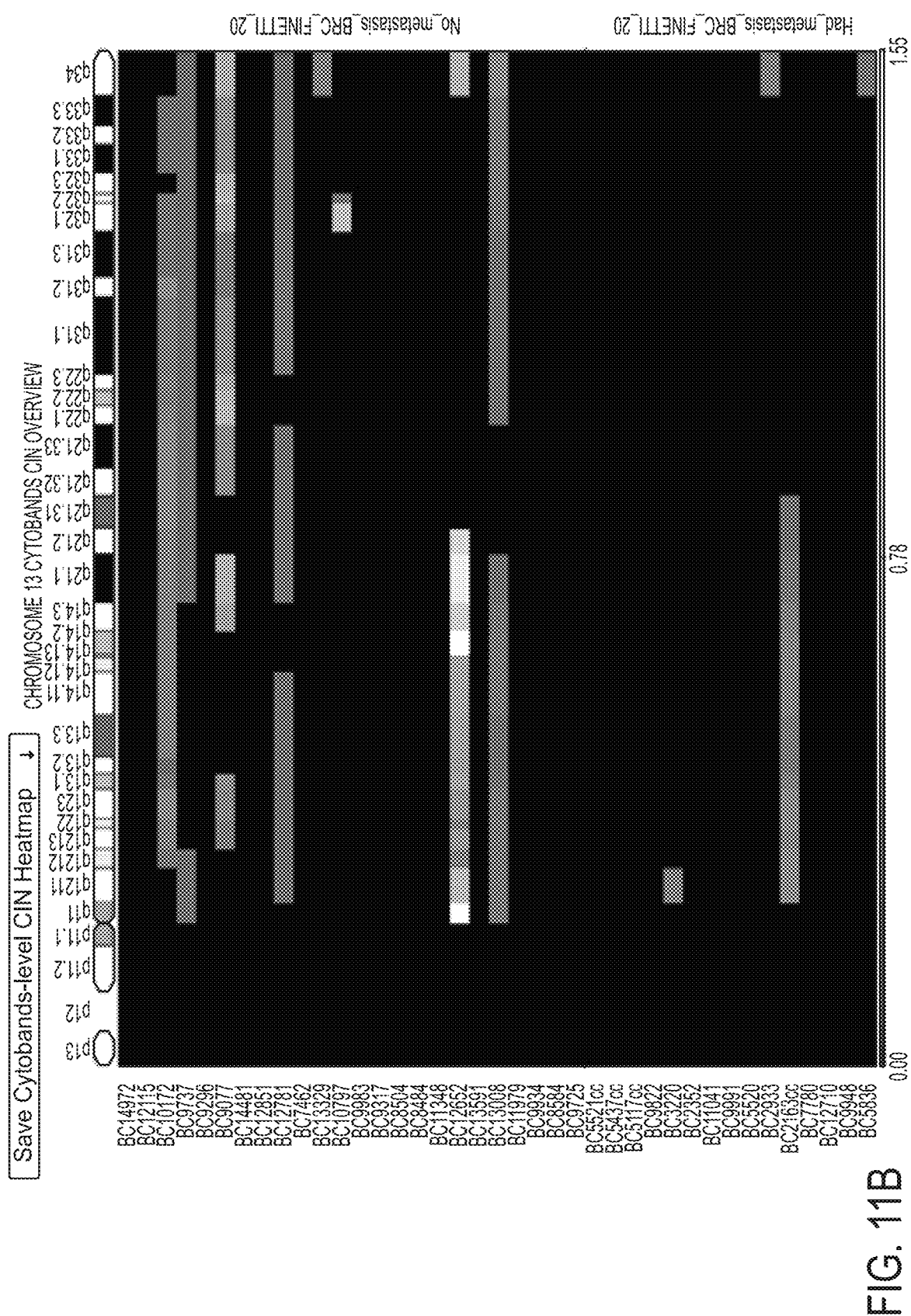

It is also possible to build a (heatmap-like) graphical display interface embedded in the browser. FIG. 11A shows a chromosome-level view. FIG. 11B shows a cytoband-level view.

Next-generation sequencing (NGS): Over the past three years, massively parallel DNA sequencing platforms have become widely available, reducing the cost of DNA sequencing by over two orders of magnitude, and democratizing the field by putting the sequencing capacity of a major genome center in the hands of individual investigators. These new technologies are rapidly evolving, and near-term challenges include the development of robust protocols for generating sequencing libraries, building effective new approaches to data-analysis, and often a rethinking of experimental design. Next-generation DNA sequencing has the potential to dramatically accelerate biological and biomedical research, by enabling the comprehensive analysis of genomes, transcriptomes and interactomes to become inexpensive, routine and widespread, rather than requiring significant production-scale efforts. The field of DNA sequencing technology development has a rich and diverse history. Over the past five years, the incentive for developing entirely new strategies for DNA sequencing has emerged on at least four levels, undeniably reinvigorating this field. This is called "Next generation sequencing" data.

To exemplify the powerful integration that the preferred embodiment provides to analyze large molecular and clinical datasets, we demonstrate here how a user could generate and validate a scientific hypothesis using this system. In this example, we will test the hypothesis that there are reproducible gene expression differences that can be identified between recurrent and non-recurrent estrogen receptor positive (ER+) tumors in Tamoxifen-treated, node-negative breast tumors. The web tool permits us to perform this analysis quickly and easily using nothing but a collection of publicly available data sets obtained from the biomedical literature. This exercise will include identification of a molecular profile in one public study [27] and its validation in another [28].

1. Can we identify, within each data set, two Tamoxifen-only treated patient cohorts that are ER+, irrespective of nodal status, have uniform gene expression array data available in the database, but differ only by whether they recurred within 5 years or did not? Users can specify these criteria in a clinical data search form to create two (or more) lists of patients that meet these criteria (see list 1200 in FIG. 12). These two cohorts frame the question posed above; other clinical considerations that are part of the published data could also have been added to the stratification. Upon saving, both sets of patient lists will be immediately available in the "Saved Lists" section, and they can be revisited at any time.

2. Are there clear molecular signatures that are distinct between these two patient cohorts (recurrent; non-recurrent)? Selecting the cohorts to compare, the optimal statistical parameters to utilize, and the experimental data set to be used, are all needed to fully configure the analysis that will be run (FIG. 13A, interface 1302). Output of this analysis is a list of annotated probes, filtered by the input specifications, which differentiate between the patient cohorts in the first (training) data set (FIG. 13B, interface 1304); output comes in a sortable table. Visualization through an expression heatmap generated by a modified Java Treeview [12] is supported, permitting the investigator to easily view the results of his/her search to ensure scientific validity of the separation and, if desired, select a subset of the probes to examine in more detail. The saved list of probes identified in this group comparison analysis can be used as the input variables in a principle component analysis (PCA) classification test [29] (FIG. 12). PCA can be used to determine if the data are linearly separable in the two dimensional data space defined by the top two principal components. The list of reporters generated can also be used to probe the validation data set in [28], to explore reproducibility of the results from the training data set.

3. Explore the reporter list to identify genes that are transcription factors and that potentially regulate the effects of tamoxifen treatment. After identification of a probe list that shows efficacy in separating Tamoxifen-treated, ER+, node negative breast cancer patients who recur from those who do not, it is expected that some additional examination of these genes would be undertaken to probe the biological mechanism and validity of any new discovery. For example, the top-scoring gene on the Loi, 2008 group comparison (FIG. 7B), MYBL1 is a known regulator of transcription [30].

Figure 14:
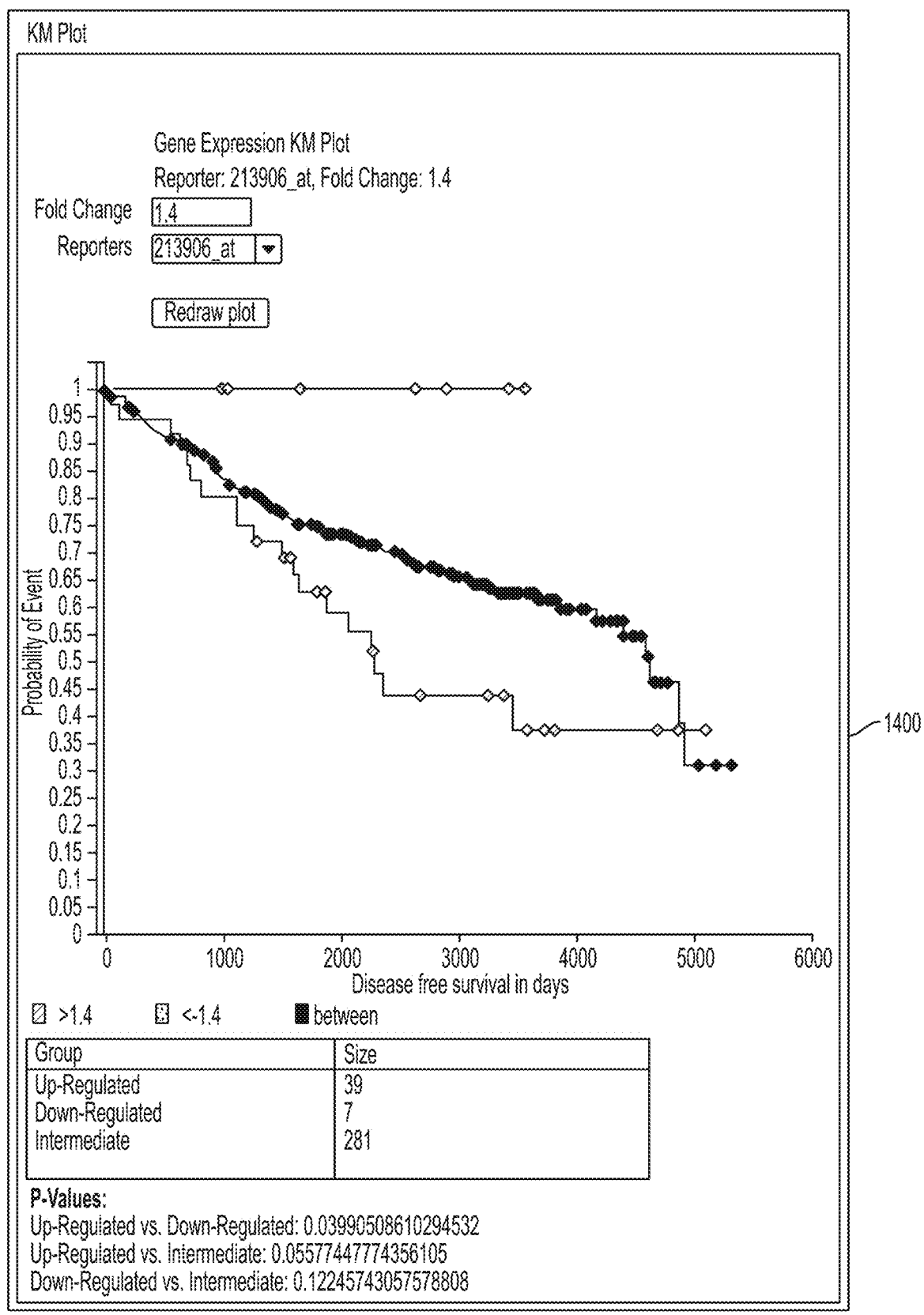
FIG. 14 shows an analysis of whether upregulation of MYBL1 impacts survival in these patient cohorts.

4. Does upregulation of MYBL1 impact survival in these patient cohorts? From the reporter list, this gene can be selected to generate a Kaplan-Meier [31] plot based on disease-free survival parameter for these patients. As can be seen in the interface 1400 of FIG. 14, there is a statistically significant ($p<0.05$; log rank test) separation between samples with 1.4 fold upregulated vs. downregulated MYBL1.

5. In the face of this information, can even more detailed analysis of the role of this gene in cancer biology be undertaken through links to external data resources? The entire list of genes identified in this analysis, or similar searches, can be visualized as a whole using the Cytoscape viewer [13] and integrated to retrieve all the Cancer Gene Index data (https://wiki.nci.nih.gov/display/ICR/Cancer+Gene+Index+End+User+Documentation) available for the set of genes, including their degree of interconnectedness. Within the flexible and powerful Cytoscape viewer, it is possible to explore groups of genes and biological concepts, or conversely to focus in detail on one gene of interest, such as MYBL1 (FIG. 9). Users can access a number of public annotation databases through the system including the STRING database [32]. The data set in STRING shows affiliations between this top-scoring gene (MYBL1) and some others of note, including BCL2, a known regulator of apoptosis, whose overexpression is caused by MYBL1, which is in turn negatively regulated by nucleolin (not shown). Entrez, GeneCards [33], and the Protein Information Resource [34] are a small subset of resources that can be easily and directly accessed from this view (FIG. 15, interface 1500 with pop-up list of options 1502).

6. Finally, is it possible to gain a more complete understanding of this gene of interest by exploring its genomic context using the integrated genome browser? In this case, we wish to understand not only the structure of the gene, but also the features of adjacent genome regions. A number of these features are available as existing JBrowse (Skinner 2009) data tiers, including OMIM [35] data and SNPs from dbSNP [36]. In this case, we wish to take the analysis further by examining the copy number changes at the MYBL1 locus for cancer patients. Users can explore the chromosomal region around this gene of interest, which is noted to be a region of chromosomal loss for patients in a third study [37] which have CNA data already processed and loaded. Another possibility would be to use the Chromosomal Instability Index [11] to view the degree of instability between cohorts of patients at the chromosomal or cytoband level, shown here for two cohorts (in this case metastatic and non-metastatic, not the clinical parameters used in the Loi, 2008 study) from the Sircoulomb et al. data set, most quickly accessed using the Quick Start feature. In this case, MYBL1, which resides on 6q13.1, is in a region that does not show a marked difference of instability between metastatic and non-metastatic patients from the Sircoulomb et al. study.

The preferred embodiment can effectively be used to develop and test a scientific hypothesis entirely in silico, allowing more resources to be spent on further downstream validation or hypothesis refinement in the laboratory or clinic. The web portal was designed to provide powerful integrated bioinformatics capabilities to the user community, with the hope of advancing biomedical and translational research in oncology.

The portal was developed as a resource for basic and translational research, and it can greatly speed the process of discovery and validation by providing a powerful platform that supports a wide variety of data analyses and diverse exploration of results. By integrating a variety of clinical and "omics" data types, researchers can use the resources and capabilities to more effectively pursue their translational research agenda. As an illustration of the value of systems approaches used, the predictive power and robustness of biomarkers can be significantly increased by integrating transcriptome profiles with interactome data to reveal more relevant functional subnetwork modules [38]. Clearly, transcriptome and proteome analyses of collections of cancer samples combined with functional annotation and modeling of perturbations in molecular pathways and networks, have revealed useful biomarkers for the classification and diagnosis of cancer subtypes, the prognosis of patient outcomes, the prediction of treatment responses, and the identification of putative targets for drug discovery [39, 40]. The preferred embodiment provides a platform to not only interrogate individual data types, but allows for combination of data from various platforms, such as transciptomics and metabolomics, helping to identify more robust signatures of disease. By supporting easy access to valuable outside resources such as pathway networks and protein-protein interactions, the preferred embodiment can be utilized as a central hub for discovery and hypothesis generation, as well as validation, in cancer research. Secure exchange of data and analyses within this multi-institutional project team will facilitate closer interactions among researchers, and rapid exchange and testing of working hypotheses.

More than conventional medicine, Systems Medicine attracts increasing research interest in the cancer community because it offers a true paradigm shift that may efficiently lead to large, rather than incremental, advances in clinical practice [41]. Importantly, preliminary data show that inexpensive high-throughput "omics" analyses of blood and urine can predict clinical course as well as or better than traditional genomic analyses of tissues (unpublished result, manuscript under preparation). Integrative and systems medicine platforms are critical to facilitating the eventual use of "omics" data to drive innovative advances in personalized clinical care and improve the quality and quantity of life for cancer patients. As part of the exploration of this long-term trend, global "omics" profiling studies from a variety of high-throughput technologies are providing comprehensive surveys of molecular changes that are involved in the occurrence and recurrence of many cancers [42]. Combined with an expected concurrent increase in the availability of clinical, pathology and outcome information from hospital medical center Electronic Health Records (EHR) systems, data form omics studies are expected to provide an unprecedented opportunity for the advancement of clinical practice. In the near future, physicians will be able to integrate and explore these datasets to understand the heterogeneity of cancers, and more efficiently identify diagnostic and prognostic markers. As this paradigm shift becomes more accepted, demand from physician researchers to navigate seamlessly between the phenotypic and genotypic characteristics of a patient, to better tailor their treatment plans, will likewise markedly increase.

Finally, as these large datasets become available for research and to inform clinical practice, it is anticipated that an even bigger challenge will arise, the desire to explore and understand how the cancer genome functions as a complex biological system in individual patients in relationship to environment, lifestyle, and genetic heritability. New tools will be needed to support these requirements and can be integrated into the preferred embodiment.

While Systems Biology will provide the foundation for a practice of Systems Medicine in the future that will be predictive, personalized, preventive, and participatory [43], it needs to be optimally integrated with healthcare management systems, imaging centers, and biobanks, as well as subjected to updated ethical regulations, review, and oversight to produce an effective regimen [44]. This will require dedicated efforts of interdisciplinary experts and special attention to clinical practice and education. Platforms such as the preferred embodiment are one part of the systems medicine puzzle to extract knowledge from various types of data and present them to multi-disciplinary teams to provide a medium of communication among them.

The preferred embodiment was designed and engineered to be a unique resource for translational cancer research that fills critical gaps in the existing research space. It integrates clinical, transcriptomic, metabolomic and systems level analysis into a single platform. While Oncomine [45] provides biologist-friendly data mining, the focus of this resource is primarily on cancer transcriptome data, and unlike the preferred embodiment, many of the cancer datasets and features of Oncomine require an annual subscription fee, rather than being freely provided. ArrayExpress [16], the Stanford Microarray Database (SMDB) [46], and the Gene Expression Omnibus [15] repositories have proven to be highly valuable in standardizing and distributing cancer microarray data, but these resources do not well support data analysis, data mining, or systems level analysis. They also focus primarily on microarray data, rather than the range of non-array "omics" data types, such as mass spectrometry metabolomics data, present in the preferred embodiment. In summary, the preferred embodiment is a unique resource for cancer data and integrative analysis and is currently available freely to the cancer research community.

The present invention provides a way of establishing a robust and comprehensive Systems Medicine platform that can directly impact healthcare delivery in the clinical setting by providing more effective clinical decision support. An additional challenge for the future will be to use decision support tools to improve quality of life even when improved health outcomes are not possible, such as in palliative care [47]. The preferred embodiment provides the means by which an array of existing and emerging "omics" data can be marshaled to improve the outcome for individual patients, and subsequent integration with EHRs can be added based on its expected impact on both clinical research and clinical practice.

While a preferred embodiment of the present invention has been set forth in detail, those skilled in the art who have reviewed the present disclosure will readily appreciate that other embodiments can be realized within the scope of the invention. For example, other data types can be normalized. Therefore, the present invention should be construed as limited only by the appended claims.

What is claimed is:

1. A method for providing data relating to cancer, the method comprising:
(a) receiving, into a processing device, raw data of a plurality of data types selected from the group consisting of mRNA expression data, miRNA expression data, metabolomics data, DNA copy number data, and next-generation sequencing;
(b) in the processing device, normalizing the raw data into normalized data of a single data type, wherein said normalization comprises background correction, normalization between arrays, and offset, wherein the offset is calculated to shrink log ratios to zero at lower intensities to reduce variability of the log ratios for low intensity spots;
(c) storing the normalized data in a database, wherein said database is comprised of a correlation of the plurality of data types to clinical outcomes, wherein the normalized data are pre-processed and mapped to existing data structures prior to storage in said database;
(d) receiving a query for the data from a device used by a user into the database;
(e) performing the query through the normalized data in the database to locate the data; and
(f) outputting the data from the database to the device used by the user, wherein said output is comprised of a personalized clinical outcome comprising a cytobands display and a heatmap view.

2. The method of claim 1, wherein step (d) comprises providing a search interface to the device used by the user.

3. The method of claim 2, wherein the search interface comprises at least one selection option for allowing the user to make a selection, and wherein step (e) comprises performing the query in accordance with the selection made by the user.

4. The method of claim 3, wherein the at least one selection option comprises at least one of a selection option relating to a cancer type and a selection option relating to an outcome.

5. The method of claim 2, wherein the search interface is configured to accept entry of a search term by the user, and wherein step (e) comprises performing the query in accordance with the search term.

6. The method of claim 5, wherein the search term relates to at least one of a gene, a rotein, a cancer type, an investigator, and an author.

7. The method of claim 1, wherein step (f) comprises performing data analysis on the data and displaying a result of the data analysis to the device used by the user.

8. The method of claim 7, wherein the data analysis comprises a data analysis selected from the group consisting of differential expression analysis, heatmaps and hierarchical clustering, principal components analysis, survival analysis, gene-disease, gene-compound, gene-protein interaction networks, and Chromosomal Instability (CIN) index calculations.

9. The method of claim 7, wherein the result of the data analysis is displayed graphically.

10. The method of claim 7, wherein step (f) further comprises mapping the result of the data analysis onto a human genome browser and displaying a result of the mapping to the device used by the user.

11. A system for providing data relating to cancer, the system comprising:
a processing device configured for receiving raw data of a plurality of data types selected from the group consisting of mRNA expression data, miRNA expression data, metabolomics data, DNA copy number data, and next-generation sequencing and normalizing the raw data into normalized data of a single data type, wherein said normalizing comprises background correction, normalization between arrays, and offset, wherein the offset is calculated to shrink log ratios to zero at lower intensities to reduce variability of the log ratios for low intensity spots; and
a database configured for storing the normalized data, receiving a query for the data from device used by a user, performing the query through the normalized data to locate the data, and outputting the data to the device used by the user, wherein said database is comprised of a correlation of the plurality of data types to clinical outcomes comprising a cytobands display and a heatmap view, and wherein the normalized data are preprocessed and mapped to existing data structures prior to storage in said database.

12. The system of claim 1, wherein the database is further configured for providing a search interface to the device used by the user.

13. The system of claim 12, wherein the database is configured such that the search interface comprises at least one selection option for allowing the user to make a selection, and wherein the database is further configured for performing the query in accordance with the selection made by the user.

14. The system of claim 13, wherein the database is configured such that the at least one selection option comprises at least one of a selection option relating to a cancer type and a selection option relating to an outcome.

15. The system of claim 12, wherein the database is configured such that the search interface accepts entry of a search term by the user, and wherein the database is further configured or performing the query in accordance with the search term.

16. The system of claim 15, wherein the database is configured such that the search term relates to at least one of a gene, a protein, a cancer type, an investigator, and an author.

17. The system of claim 11, wherein the database is configured for performing data analysis on the data and displaying a result of the data analysis to the device used by the user.

18. The system of claim 17, wherein the database is configured such that the data analysis comprises a data analysis selected from the group consisting of differential expression analysis, heatmaps and hierarchical clustering, principal components analysis, survival analysis, genedisease, gene-compound, gene-protein interaction networks, and Chromosomal Instability (CIN) index calculations.

19. The system of claim 17, wherein the database is configured such that the result of the data analysis is displayed graphically.

20. The system of claim 17, wherein the database is configured for mapping the result of the data analysis onto a human genome browser and displaying a result of the mapping to the device used by the user.

* * * * *